United States Patent
Zasadzinski et al.

(10) Patent No.: US 6,565,889 B2
(45) Date of Patent: May 20, 2003

(54) BILAYER STRUCTURE WHICH ENCAPSULATES MULTIPLE CONTAINMENT UNITS AND USES THEREOF

(75) Inventors: Joseph A. Zasadzinski, Santa Barbara, CA (US); Scott A. Walker, White Bear Lake, MN (US); Michael T. Kennedy, Oak Park, CA (US); Edward T. Kisak, Santa Barbara, CA (US); Bret A. Coldren, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/842,240

(22) Filed: Apr. 24, 2001

(65) Prior Publication Data

US 2002/0061331 A1 May 23, 2002

Related U.S. Application Data

(63) Continuation-in-part of application No. 09/139,045, filed on Aug. 24, 1998, now Pat. No. 6,221,401, which is a continuation-in-part of application No. 08/980,332, filed on Nov. 28, 1997, now abandoned.
(60) Provisional application No. 60/245,701, filed on Nov. 2, 2000, and provisional application No. 60/032,306, filed on Dec. 2, 1996.

(51) Int. Cl.[7] ............... A61K 9/14; A61K 9/16; A61K 9/50
(52) U.S. Cl. .............. 424/490; 424/423; 424/427; 424/430; 424/434; 424/435; 424/436; 424/444; 424/450; 424/451; 424/464; 424/449
(58) Field of Search .............. 424/490, 423, 424/427, 430, 434, 435, 436, 444, 450, 489, 498

(56) References Cited

U.S. PATENT DOCUMENTS

| | | | |
|---|---|---|---|
| 4,078,052 A | 3/1978 | Papahadjopoulos | |
| 5,004,566 A | 4/1991 | Schnur et al. | 260/403 |
| 5,492,696 A | 2/1996 | Price et al. | 424/417 |
| 5,618,560 A | 4/1997 | Bar-Shalom et al. | 424/486 |
| 5,643,574 A | 7/1997 | Gould-Fogerite et al. | 424/184.1 |
| 5,723,147 A | 3/1998 | Kim et al. | |
| 5,855,911 A * | 1/1999 | Lopez-Berestein et al. | 424/450 |
| 6,045,955 A | 4/2000 | Vincent | |

OTHER PUBLICATIONS

Allen, T. M., *Current Opinion in Colloid and Interface Science* 1, 645–651 (1996) (Exhibit 32).
Lasic, D. D. et al., *Current Opinion in Solid State and Materials Science*, 1, 392–400 (1996) (Exhibit 33).
Whitesides, T. H. and Ross *J. Colloid and Interface Science*, 169, 48–59 (1995) (Exhibit 34).
Zasadzinski, J. A., *Current Opinion in Solid State and Materials Science* 2, 345–349 (1997) (Exhibit 35).
Chiruvolu, Shivkumar et al., "Higher Order Self–Assembly of Vesicles by Site–Specific Binding," *Science*, 264:1753–1756. Jun. 17, 1994. (Exhibit 6).
Papahadjopoulos, D. et al, "Effects of Proteins on Thermotropic Phase Transitions of Phospholipid Membranes," *Biochimica et Biophysica Acta*, 401:317–335. 1975. (Exhibit 7).

(List continued on next page.)

*Primary Examiner*—James M. Spear
(74) *Attorney, Agent, or Firm*—Mandel & Adriano

(57) ABSTRACT

The present invention provides compositions and methods of preparing a bilayer structure for encapsulating multiple containment units. These containment units can contain therapeutic, diagnostic agents or imaging agents that can be released through the bilayer structure. A suitable example of such a containment unit is a unilamellar or multilamellar vesicle.

39 Claims, 13 Drawing Sheets

OTHER PUBLICATIONS

Papahadjopoulos, D. et al, "Cochleate Lipid Cylinders: Formation by Fusion of Unilamellar Lipid Vesicles," *Biochimica et Biophysica Acta*, 394:483–491. 1975. (Exhibit 8).

Papahadjopoulos, D. et al, "Induction of Fusion in Pure Phospholipid Membranes by Calcium Ions and Other Divalent Metals," *Biochimica et Biophysica Acta*, 448:265–283. 1976. (Exhibit 9).

Freireich, Emil J. et al, "Quantitative Comparison of Toxicity of Anticancer Agents in Mouse, Rat, Hamster, Dog, Monkey, and Man," *Cancer Chemotherapy Reports*, 50(4):219–244. May 04, 1966. (Exhibit 10).

Ahl, P. L., et al. *Biochimica et Biophysica Acta* 1195, (1994), 237–244. (Exhibit 11).

Allen, T. M. et al., *Advanced Drug Delivery Reviews*, 16, (1995), 267–284. (Exhibit 12).

Boni, L.T. et al., *Biochim. Biophys. Acta*, 1146, (1993), 247–257. (Exhibit 13).

Cullis, P.R. et al., *Biochim. Biophys. Acta*, 1997, 1331, 187–211. (Exhibit 14).

Emans, N. et al., *Biophysical Journal*, 69, (1995), 716–728. (Exhibit 15).

Jung, H.T. et al, *Proc. Natl. Acad. Sci. USA*, 2001, 98, 1353–1357. (Exhibit 16).

Kim, T., S. Murdande, A. Gruber, S. Kim, *Anesthesiology* 85, (1996), 331–338. (Exhibit 17).

Leckband, D. E. et al., *Biochemistry*, 33, (1994), 4611–4624. (Exhibit 18).

Leckband, D. et al., *Biophys. J.*, 69, (1995), 1162–1169. (Exhibit 19).

Leckband, D. et al., *Nature*, 376, (1995), 617–618. (Exhibit 20).

Loughrey, H. C. et al., *Biochim. Biophys. Acta*, 1028, (1990), 73–81 (Exhibit 21).

Mayer, E. (1985) *J. Microsc.* 140, 3–15. (Exhibit 22).

Noppl–Simson, D.A. et al., *Biophysical Journal*, 70, (1996), 1391–1401. (Exhibit 23).

Papahadjopoulos, D., et al., (1974) *Biochim. Biophys. Acta*, 401, 317–335. (Exhibit 24).

Simon, S.A., and McIntosh, T.J. (1984) *Biochim. Biophys. Acta*, 773, 169–172. (Exhibit 25).

Walker, S. A. et al., *Nature*, 387, (1997), 61–64. (Exhibit 26).

Zasadzinski, J. A. i et al., *J. Electron Microsc. Technique*, 13, (1989), 309–334. Exhibit 27).

Zasadzinski, J.A. et al., *Current Opinion in Colloid and Interface Science*, 2001, 6, 89–90. (Exhibit 28).

Kisak, E., et al. *Langmuir* 16, 2825–2831. (2000) (Exhibit 29).

Spector, M. S., J. A. Zasadzinski, M. B. Sankaram, *Langmuir* 12, 4704–4708. (1996) (Exhibit 30).

Walker, S. A. et al., *Langmuir*, 13, 5076–5081. (1997) (Exhibit 31).

* cited by examiner

FIG. 4
EXAMPLE 1 PROCESS
BIOTIN-LABELLED VESICLES
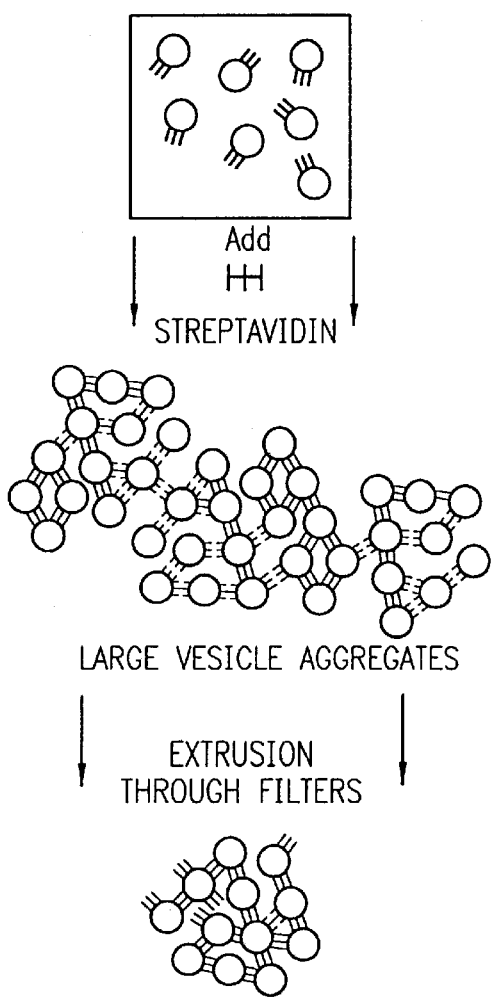
EXAMPLE 2 PROCESS
BIOTIN-LABELLED VESICLES
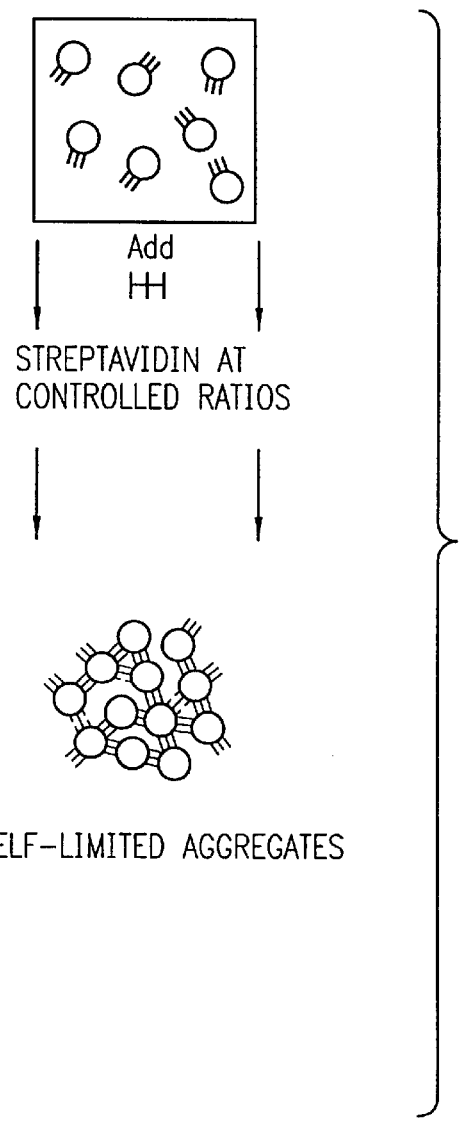

BILAYER STRUCTURE WHICH ENCAPSULATES MULTIPLE CONTAINMENT UNITS AND USES THEREOF

This application claims the priority of provisional application, U.S. Serial No. 60/245,701, filed Nov. 2, 2000 and is a continuation-in-part application of U.S. Ser. No. 09/139,045, filed Aug. 24, 1998, U.S. Pat. No. 6,221,401 which is a continuation-in-part application of U.S. Ser. No. 08/980,332, filed Nov. 28, 1997, now abandoned which claims the priority of provisional application, U.S. Serial No. 60/032,306, filed Dec. 2, 1996, all of which are incorporated herein, in their entirety, by reference.

This invention was made with Government support under NSF grant DMR-9123048 and NIH grant GM47334. The Government has certain rights in this invention.

Throughout this application various publications are referenced. The disclosures of these publications in their entireties are hereby incorporated by reference into this application, in order to more fully describe the state of the art to which this invention pertains.

BACKGROUND OF THE INVENTION

Conventional drug delivery technology, which in the past has concentrated on improvements in mechanical devices, such as implants or pumps, to achieve more sustained release of drugs, is now advancing on a microscopic and even molecular level. Recombinant technology has produced a variety of new potential therapeutics in the form of peptides and proteins, and these successes, have spurred the search for newer and more appropriate delivery and targeting methods and vehicles.

Microencapsulation of drugs within biodegradable polymers and liposomes has achieved success in improving the pharmacodynamics of a variety of drugs, such as antibiotics and chemotherapeutic agents [J. A. Zasadzinski, *Current Opinion in Solid State and Materials Science* 2, 345 (1997); D. D. Lasic, D. Papahadjopoulos, *Current Opinion in Solid State and Materials Science* 1, 392 (1996); D. D. Lasic, *Liposomes: From Physics to Applications* (Elsevier, Amsterdam (1993); T. M. Allen, *Current Opinion in Colloid and Interface Science* 1, 645 (1996)]. These drug delivery structures are designed to encapsulate a drug efficiently inside a polymer or lipid shell, and are administered to the patient. The drug delivery vehicles are sometimes either actively or passively targeted so that they release their entrained drug at a specific target site in the body. This targeted release of a drug has been shown to increase the effectiveness of the encapsulated drug and decrease the adverse side effects typically seen when administering the free drug. For example, unilamellar vesicles are currently used as drug delivery vehicles for a number of compounds where slow, sustained release or targeted release to specific sites in the body is desired. The drug to be released is contained within the aqueous interior of the vesicle and release is achieved by slow permeation through the vesicle bilayer. A variety of modifications of the unilamellar vesicle membrane have been attempted, including polymerizing, or crosslinking the molecules in the bilayer, to enhance stability and reduce permeation rates, and incorporating polymers into the bilayer, to reduce clearance by macrophages in the bloodstream.

There are several examples of drug delivery systems that have been developed. One example of such a vesicle structure is known as Depofoam™ (i.e. Multivesicular Liposome (MVL)) [J. A. Zasadzinski, *Current Opinion in Solid State and Materials Science* 2, 345 (1997); M. S. Spector, J. A. Zasadzinski, M. B. Sankaram, *Langmuir* 12, 4704 (1996); T. Kim, S. Murdande, A. Gruber, S. Kim, *Anesthesiology* 85, 331 (1996)]. Depofoam™ is a multivesicular particle that is created by multiple emulsification steps. A defined lipid composition is dissolved in a volatile solvent. The dispersed lipids in the solvent are vigorously mixed with water to form a first emulsion, designated a solvent continuous emulsion. This first emulsion is then added to a second water/solvent emulsion and emulsified to form a water in solvent in water double emulsion. The solvent is removed from the mixture, resulting in discrete, foam-like spherical structures consisting of bilayer-separated water compartments. The minimum size of these structures is about 5 to 10 microns. Depofoam™ particles do not include a distinct bilayer structure that encapsulates the multivesicular particles, i.e. there are no individual, distinct interior vesicles. Therefore, the interior compartment must share the bilayer walls. Because of the emulsification in solvents, these Depofoam™ particles are not capable of encapsulating existing vesicles, or sensitive biological materials, that degrade or denature in the presence of solvent. Production of these particles also requires high shear rates to promote emulsification. Such shear rates would degrade many biological macromolecules.

Liposomes are sealed, usually spherical, either unilamellar or multilamellar vesicles that are capable of encapsulating a variety of drugs. Liposomes are the most widely studied vesicles to date and they can be formulated with a variety of lipid and compositions that can alter their stability, pharmacokinetics and biodistribution [T. M. Allen et al., *Adv. Drug Deliv. Rev.*, 16, 267–284 (1995)]. The lipid bilayer acts to encapsulate a drug and control its release rate. Liposomes typically include polymers inserted into the vesicle membrane in order to shield the liposomes from macrophages attempting to clear foreign objects from the body. These polymers greatly enhance the circulation time of liposomes. Liposomes can also incorporate specific binding agents on their surface in order to try to target the vesicles to a specific target organ or cell type.

A disadvantage of both multilamellar and unilamellar liposomes as delivery systems is their size, which prevents them from crossing most normal membrane barriers and limits their administration by the intravenous route. In addition, the tissue selectivity of liposomes is typically limited to the reticuloendothelial cells, which recognize them as foreign microparticulates and then concentrate the liposomes in tissues, such as the liver and spleen. A further disadvantage of the liposome system is its reliance on a single lipid membrane for controlling drug encapsulation, drug permeability, and liposome biocompatibility. It has proven quite difficult to find lipid membranes able to carry out all these tasks effectively.

Polymers have also been used as drug delivery systems. Polymer structures similar to lipid vesicles are prepared carrying an entrained drug, such as Prolease and Medisorb (Alkermes, Inc). They generally release drugs by (1) polymeric degradation or chemical cleavage of the drug from the polymer; (2) swelling of the polymer to release drugs trapped within the polymeric chains; (3) osmotic pressure effects, which create pores that release a drug which is dispersed within a polymeric network; and/or (4) simple diffusion of the drug from within the polymeric matrix to the surrounding medium.

With the drawbacks of the currently available microencapsulation vehicles, there remains a need to produce better and more efficient microencapsulation vehicles to enhance drug delivery. The present invention is directed to meeting these and other challenges.

SUMMARY OF THE INVENTION

The present invention provides novel vesosome compositions having a bilayer structure for encapsulating multiple containment units, such as multilamellar or unilamellar vesicles, polymer spheres, DNA complexes, micelles, emulsion droplets or other submicroscopic particles. These multiple containment units can contain drugs, imaging agents, DNA, emulsions, colloidal particles, enzymes, cosmetics, proteins and other diagnostic and therapeutic agents.

Further, the present invention provides a variety of new methods for encapsulating containment units, such as lipid vesicles, within an outer encapsulating bilayer membrane, and methods of controlling the number of exterior bilayers, the organization of the interior vesicles or biological materials inside the vesicles, and the structure of the encapsulating bilayer membrane. The invention further provides encapsulation methods for encapsulating both multiple individual containment units and aggregated containment units.

The encapsulating bilayer membranes of the invention can be either unilamellar or multilamellar, and are made of a variety of lipid compositions. Complex multiple chamber encapsulating structures can also be created. The size of the encapsulating bilayer membrane can be controlled either by manipulating the lipid composition of the membrane or by mechanical processing.

The encapsulated containment units (e.g. vesicles) can either be of uniform size and composition or of varied size and composition. They can be unilamellar or multilamellar. The vesicles can vary in size (as long as they are smaller than the encapsulating outer bilayer membrane structure) and can either be free-floating or aggregated to one another by ligand-receptor, antibody-antigen, or electrostatic or covalent chemical interactions. Other free-floating or aggregated colloidal particles or biological macromolecules can be encapsulated in a similar fashion.

Furthermore, the encapsulating bilayer membrane can either attach to the vesicles, vesicle aggregates, colloidal particles, colloidal aggregates, or biological macromolecules by ligand-receptor, antibody-antigen, or electrostatic or covalent chemical interactions, or the encapsulating bilayer membrane can be used to encapsulate vesicles passively i.e. without the aid of any attractive interaction. The encapsulating bilayer membrane can further be loaded with polymer lipids, or site-specific antigens (or other recognition molecules), to increase the effectiveness of drug delivery.

The exterior encapsulating bilayer membranes can regulate the permeation of the interior contents, of the containment units, at a variety of rates due to the multiple membrane permeation barriers that can be established by employing different lipid compositions. The membrane barriers of the containment units and the encapsulating bilayer membrane can also protect the interior contents from destabilizing factors such as degradation, shear, etc.

By optimizing both the exterior bilayer membrane structure and the interior containment unit compositions, the size and size distribution of the interior containment units, the overall size of the vesosome, the nature of the attachments of the interior containment units, and the type of additives to the outer bilayer membrane (such as polymers or specific recognition sites), an extremely versatile drug delivery system can be developed for a variety of applications.

BRIEF DESCRIPTION OF THE DRAWINGS

FIG. 4 is a schematic diagram of the processes, as described in Examples 1 and 2, infra.

DETAILED DESCRIPTION OF THE INVENTION

Figure 1:
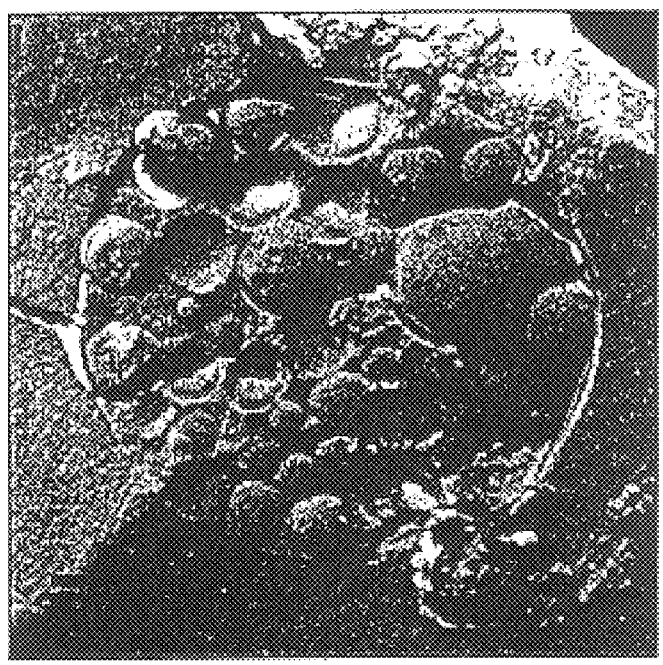
FIG. 1 is a freeze-fracture transmission electron micrograph of a typical vesosome of the invention prepared upon mixing cochleated cylinders with sized vesicle aggregates (at a 1:1 mole ratio) prior to the addition of EDTA. There is only one outer bilayer, and the interior vesicles appear to be specifically aggregated.

Definitions:

As used in this application, the following words or phrases have the meanings specified.

As used herein, the term "containment unit" means any structure having an internal space that can be occupied by an agent such as a therapeutic, diagnostic, cosmetic or imaging agent. Typically, the structure is spherical, but is not necessarily so. An example of a containment unit is a lipid vesicle.

As used herein the term "vesosome" is a structure formed by multiple unilamellar or multilamellar containment units (e.g. vesicles) encapsulated within a distinct, outer lipid bilayer membrane structure.

As used herein "uniform size" means of approximately similar size. It does not necessarily mean vesicles having an identical size.

As used herein, "biological agent" means drugs, solutes, therapeutic agents, diagnostic agents and/or imaging agents.

In order that the invention herein described may be more fully understood, the following description is set forth.

Compositions of the Invention

The invention provides for compositions including a vesosome structure having an outer lipid bilayer membrane for encapsulating interior multiple containment units, such as lipid vesicles. The outer bilayer membrane can be produced from a variety of lipid compositions. The bilayers can be multilamellar or unilamellar.

The interior containment units within the bilayer structure can be of a uniform size and of similar membrane or interior composition, or can be of varied size and/or different membrane or interior compositions. The membrane of the interior containment units can be unilamellar or multilamellar. The containment units can be aggregated (S. Chiruvolu et al. (1994) Science 264:1753) or free. The characteristics of the outer bilayer structure and the multiple containment units are determined during the production process described below.

Typically, the vesosome of the invention is submicroscopic in size. The size of the vesosome can be controlled from about 0.05 micron to >5 micron in diameter, by manipulating the lipid composition of the outer bilayer membrane or by mechanical processing, for example by extrusion of the vesosomes through filters of defined sizes. The vesosome can incorporate a variety of water or lipid soluble drugs or other solutes within the interior vesicles, or within the exterior capsule (i.e. the space between the vesicles and the outer bilayer membrane, or both. These drugs or other soluble materials can then permeate slowly through the interior vesicle membrane and exterior bilayer membranes, providing a controlled, slow release of materials over time.

Methods for Making and Using Compositions of the Invention

The invention further provides methods for making the compositions of the invention, including encapsulating multiple containment units within an outer bilayer membrane (i.e. a vesosome).

In general, the vesosome of the invention can be prepared by a multi-step process. The first step is making the interior containment units and loading the specific drug or other agent to be delivered. A second step involves creating a controlled-size vesicle aggregate, if aggregated vesicles are used, without disrupting the vesicle bilayer or contents. The third step is encapsulating the free or aggregated vesicles within an outer membrane.

The outer bilayer membrane of the vesosome is generated from the transformation of "open" lipid bilayer structures, such as cochleated cylinders [Papahadjopoulos, D., et al., (1974) *Biochim. Biophys. Acta,* 401, 317–335; Papahadjopoulos, D., et al., (1975) *Biochim. Biophys. Acta,* 394, 483–491; Papahadjopoulos, D., et al., (1976) *Biochim. Biophys. Acta,* 448, 265–283] or interdigitated sheets [Simon, S. A., and McIntosh, T. J., (1984) *Biochim. Biophys. Acta,* 773, 169, and Boni, L. T. et al., (1993) *Biochim. Biophys. Acta,* 1146, 237], to create the outer bilayer membrane structures of the invention, which encapsulate the multiple containment units.

Open lipid bilayers are structures that form an open conformation and can transform to the closed bilayer structure, which encapsulates multiple containment units. Open lipid bilayers are characterized by their properties, such as rigid, gel, or "frozen chain" bilayer lipid phases that do not form closed structures spontaneously, but rather form lipid bilayer stacks or rolls in aqueous solution. Alternatively, the open lipid bilayers can be those structures that are in "closed" conformation, which can be induced to an open conformation and can transform to the bilayer structure, which encapsulates multiple containment units.

Cochleated cylinders can be made from phosphotidylserine or phosphotidylglycerol complexed with calcium. Interdigitated sheets can be made from a variety of neutral or charged lipids and surfactants that form the lamellar bilayer phase at low temperatures. Examples of suitable lipids include, but are not limited to, dipalmitoyl-, dimyristoyl-, distearanoyl-, phosphotidylcholines, or phosphotidylglycerols, with and without cholesterol, or with and without DPPE-polyethylene glycol. An example of a suitable surfactant is dihexadecylphosphate, which also forms interdigitated sheets.

Examples of suitable neutral lipids include but are not limited to 1,2-caproyl-sn-glycero-3-phosphocholine, 1,2-heptanoyl-sn-glycero-3-phosphocholine, 1,2-capryloyl-sn-glycero-3-phosphocholine, 1,2-nonanoyl-sn-glycero-3-phosphocholine, 1,2-capryl-sn-glycero-3-phosphocholine, 1,2-undecanoyl-sn-glycero-3-phosphocholine, 1,2-lauroyl-sn-glycero-3-phosphocholine, 1,2-tridecanoyl-sn-glycero-3-phosphocholine, 1,2-myristoyl-sn-glycero-3-phosphocholine, 1,2-pentadecanoyl-sn-glycero-3-phosphocholine, 1,2-palmitoyl-sn-glycero-3-phosphocholine, 1,2-phytanoyl-sn-glycero-3-phosphocholine, 1,2-heptadecanoyl-sn-glycero-3-phosphocholine, 1,2-stearoyl-sn-glycero-3-phosphocholine, 1,2-bromostearoyl-sn-glycero-3-phosphocholine, 1,2-nonadecanoyl-sn-glycero-3-phosphocholine, 1,2-arachidoyl-sn-glycero-3-phosphocholine, 1,2-heneicosanoyl-sn-glycero-3-phosphocholine, 1,2-behenoyl-sn-glycero-3-phosphocholine, 1,2-tricosanoyl-sn-glycero-3-phosphocholine, 1,2-lignoceroyl-sn-glycero-3-phosphocholine.

Examples of suitable charged lipids include, but are not limited to, 1,2-diacyl-3-trimethylammonium-propane, 1,2-dimyristoyl-3-trimethylammonium-propane, 1,2-dipalmitoyl-3-trimethylammonium-propane, 1,2-distearoyl-3-trimethylammonium-propane, 1,2-diacyl-3-dimethylammonium-propane, 1,2-dimyristoyl-3-dimethylammonium-propane, 1,2-dipalmitoyl-3-dimethylammonium-propane, and 1,2-distearoyl-3-dimethylammonium-propane.

Polymers such as polyethylene glycol linked to lipids, can be incorporated into the vesicle membrane to sterically stabilize the vesosome against aggregation and/or clearance by macrophages. These various processes can be optimized for a particular drug release or other application.

The aggregated or free containment units (e.g. vesicles) and open lipid bilayer are mixed in a solution under suitable conditions so that the open lipid bilayers transform to create the outer bilayer membrane structures of the invention which encapsulate the aggregated multiple containment units.

In accordance with the practice of the invention, the aggregated multiple containment units and the open lipid bilayer can be mixed in a suitable ratio, e.g., a 1:1 ratio. Other ratios are also possible.

In a further embodiment of the methods and compositions of the invention, the resulting vesosomes are encapsulated by a second outer bilayer membrane. This allows for formation of multiple vesosomes, for example, consisting of layers of membrane bilayers encapsulating multiple containment units.

In accordance with the practice of the invention, the interior multiple containment units, e.g. vesicles, can include biological material, such as a therapeutic agent. Alternatively, the units can include a diagnostic agent or an imaging agent. Moreover, the interior vesicles can contain a reactive agent, such as acid or base (Cullis, P. R. et al., Biochim. Biophys. Acta, 1997, 1331, p187) so as to create new therapeutic and/or diagnostic agents in situ. Methods for enclosing agents within the containment units (e.g., liposomes) are well known (CA 1314209; DE 3880691; GB 9605915; DE 4402867).

Suitable therapeutic agents are those which can be enclosed within a containment unit and include, but are not limited to, the following: antimicrobial agents such as antibiotics, antifungal, chemotherapeutic, angiogenesis, antimycobacterial drugs and antibodies.

Examples of antibiotics include, but are not limited to, amikacin, kanamycin B, amphomycin, bacitracin, bicyclomycin, capreomycin, polymyxin E, cycloserine, chloramphenicol, dactinomycin, erythromycin, gentamicin, gramicidin A, penicillins, rifamycins, streptomycin and tetracyclines.

The therapeutic agent can be a drug acting at synaptic and/or neuroeffector junctional sites. Examples include, but are not limited to, neurohumoral transmitters, cholinergic agonists, anticholinesterase agents, antimuscarinic drugs, agents acting at the neuromuscular junction and autonomic ganglia, catecholamines, sympathomimetic drugs and adrenergic receptor antagonists.

Alternatively, the therapeutic agent can be a drug acting on the central nervous system (CNS). Examples include, but are not limited to, antipsychotic drugs, neuroleptic drugs, tricyclic antidepressants, monoamine oxidase inhibitors, lithium salts and benzodiazepines.

Additionally, the therapeutic agent can be a drug that reduces inflammation. Examples include, but are not limited to, antagonists of histamine, bradykinin, 5-hydroxytryptamine; lipid-derived autacoids; methylxanthines, cromolyn sodium and analgesic-antipyretics.

The therapeutic agent can be a drug that affects renal function and electrolyte metabolism. Examples include, but are not limited to, diuretics and inhibitors of tubular transport of organic compounds.

In addition, the therapeutic agent can be a drug that affects cardiovascular function. Examples include, but are not limited to, renin and angiotensin; organic nitrates, calcium-channel blockers and beta-adrenergic antagonists; antihypertensive agents, digitalis, antiarrhythmic drugs and drugs used in the treatment of hyperlipoproteinemias.

Suitable diagnostic agents include, but are not limited to, radiolabels, enzymes, chromophores and fluorescers.

Suitable imaging agents include, but are not limited to, radiopharmaceutical agents. Some of the radiopharmaceutical agents currently used for imaging include nuclides such as. $^{201}Tl$, $^{99m}Tc$, $^{133}Xe$, and the like, chelates of nuclides, radiolabeled metabolic agents such as $^{11}C$-deoxy-D-glucose, $^{18}F$-2-fluorodeoxy-D-glucose, [1-$^{11}C$]- and [$^{123}I$]-beta-methyl fatty acid analogs, $^{13}N$-ammonia, and the like, infarct avid agents such as $^{99m}Tc$-tetracycline, $^{99m}Tc$-pyrophosphate, $^{203}Hg$-mercurials, $^{67}Ga$-citrate, and the like, and radiolabeled ligands, proteins, peptides, and monoclonal antibodies.

The present invention includes methods for delivering an encapsulated biological material, such as a therapeutic or diagnostic agent, to a target wound or diseased site. In these methods a vesosome of the invention is introduced to the target site where the contents of the multiple containment units are released at the target site over time. Alternatively, the methods also include delivering an agent to an intended site for cosmetic, veterinary, and other applications requiring slow continuous release (CA 1314209; DE 3880691; GB 9605915; DE 4402867).

Introduction of the vesosome to the target site can be effected by various methods. For example, the vesosome can be introduced by intramuscular injection, intravenous injection, oral administration, pulmonary adsorption, rectal administration, subcutaneous injection, sublingual administration, or topical application. Other methods of administration are possible and are known in the art.

The most effective mode of administration and dosage regimen for the biological agents in the multiple containment units of the present invention depends upon the severity and course of the disease, the subject's health and response to treatment and the judgment of the treating physician. Accordingly, the dosages of the molecules should be titrated to the individual subject.

The interrelationship of dosages for animals of various sizes and species and humans based on mg/m$^2$ of surface area is described by Ferrite, E. J., et al. (Quantitative Comparison of Toxicity of Anticancer Agents in Mouse, Rat, Hamster, Dog, Monkey and Man. Cancer Chemother, Rep., 50, No.4, 219–244, May 1966).

Adjustments in the dosage regimen can be made to optimize the response. Doses can be divided and administered on a daily basis or the dose can be reduced proportionally depending upon the situation.

Multiple Containment Units

Types of multiple containment units include, but are not limited to, multilamellar or unilamellar vesicles [Zasadzinski, J. A. et al., Current Opinion in Colloid and Interface Science, 2001, 6, 89–90], polymer spheres, DNA complexes, micelles, emulsions, or other submicroscopic particles. The vesicles can be made from a variety of phospholipids, cholesterol, fatty acids, etc.

The detailed composition and size of the interior containment units is not critical in the methods for preparing and using the vesosomes of the invention. Commonly used compositions are 60% DSPC/40% cholesterol (Lasic, D. D., Liposome: from Physics to Application, Elsevier, Amsterdam (1993)), 60% egg lecithin/40% cholesterol, dipalmitoylphosphatidylcholine (DPPC), diacylphosphotidylcholine (DLPC), and diacylphosphotidy serine (DOPS)).

Methods for making unilamellar and multilamellar vesicles are well known in the art. Detergent dialysis, sonication, spontaneous vesicle preparations, and reverse phase evaporation, are all possible methods that can be used for vesicle preparation. Various types of vesicle preparation methods can be used, including (1) chemical preparations of vesicles such as reverse phase evaporation, detergent dialysis, pH jump, (2) mechanical treatments such as ultrasonication, and (3) spontaneous vesicle preparations which lead directly to equilibrium vesicles (without special treatments) [Jung, H. T. et al, *Proc. Natl. Acad. Sci. USA,* 2001, 98, 1353]. Unencapsulated biological agents can be removed at any stage of these vesicle formation processes by various dialysis techniques, ion exchange, chromatography, filtration or centrifugation.

The steps of preparing interior vesicles and loading the drug are well known in the art (T. M. Allen et al., *Advanced Drug Delivery Reviews,* 16, 267–284 (1995); T. M. Allen, *Current Opinion in Colloid and Interface Science,* 1, 645–651 (1996); D. D. Lasic, *Liposomes: From Physics to Applications,* (Elsevier, Amsterdam (1993)); D. D. Lasic et al., *Current Opinion in Solid State and Materials Science,* 1, 392–400 (1996)).

Aggregate Vesicle Sizing

The invention further provides methods for obtaining aggregated containment units having a uniform size. The aggregation of the vesicles can be accomplished by a variety of ligand-receptor interactions (such as biotin-avidin interaction), antigen-antibody interactions, or chemical crosslinking agents that mimic ligand-receptor interactions. The vesicle aggregates can be made to a specific size or diameter as described in Example 2, infra.

An embodiment of the invention includes a method for regulating the size of multiple containment unit aggregates by preparing multiple containment units having the reactive groups (e.g. ligand such as biotin or antigen) on the surface of the multiple containment units, determining the ratio of reactive groups on the surface of the multiple containment units to crosslinking agents (e.g. receptor such as streptavidin or antibody to antigen) in solution, as described in Example 2 infra, and combining the multiple containment units having the reactive groups on the surface of the multiple containment units with crosslinking agent in the determined ratio, thereby resulting in the aggregated multiple containment units having a desired size.

A mechanical method of filtering aggregated vesicles having varying sizes through multiple filter membranes under pressure, also referred to as "extruding", can be further applied to obtain aggregated vesicles of a specific size. The vesicles may be passed through two filters, although this is not essential to the process. Generally, the filters have pores of uniform size, such as Nucleopore filters. The filtered vesicle aggregates so filtered have a substantially uniform size. For example, the filtered vesicles can have a size ranging from 0.05–5 µm in diameter.

Sizing of multiple containment unit aggregates can be accomplished by other methods such as (1) quenching the aggregation (adding another ligand that binds to the receptor, preventing it from cross-linking more vesicles), (2) using charged vesicles that will aggregate at a slower rate due to enhanced electrostatic repulsion between the vesicles and (3) altering the stoichiometric ratio of the ligand to receptor, which also can lead to a slower, controlled aggregation.

Uniform aggregate sizes can also be prepared by removing excess freely floating vesicles or small aggregates by centrifugation or dialysis techniques.

Advantages of the Invention:

The compositions and methods of the vesosomes of the invention provides several new features including:
1) Specific aggregation of containment units via ligand-receptor interactions (Chiruvolu et al., 1994);
2) Uniform sizing of containment unit aggregates via extrusion by filtration; and
3) Encapsulation of the free or aggregated containment units within a second or multiple outer bilayer membrane.

The methods of the invention allow for the encapsulation of individual or aggregated vesicles. The composition of the outer encapsulating lipid bilayer of the vesosome can be varied. The outer encapsulating lipid bilayer can include the use of biotin and streptavidin. The outer encapsulating lipid bilayer can also be loaded with specific targeting agents, such as antibodies, for targeting specific tissues in the body.

The benefits of the resulting compositions, including vesosomes, over single-walled vesicles, such as liposomes, used for drug delivery, include the division of important, but sometimes incompatible, membrane attributes. Such membrane attributes include permeation rate, membrane charge, specific recognition molecules, steric stabilizers, membrane rigidity and phase transition temperatures, all of which play a role in the optimization of a drug delivery vehicle. For example, the exterior bilayer membrane can incorporate steric stabilizer molecules, such as polyethylene glycol, or specific recognition sites, such as ligand or specific receptors for site-targeted delivery. The vesosome structure can divide necessary functions between two or more membranes rather than relying on a single membrane. The interior containment units can be of various sizes and compositions to optimize delivery of multiple drugs, or prolong delivery over time, from the vesosome.

This appears to be the first time multiple containment units, such as lipid vesicles, have been encapsulated within an outer bilayer membrane structure by a controlled and reproducible process. The exact composition of the encapsulated containment units is not important and the vesicles can be composed of a variety of different lipid compositions and lipid mixtures. Vesicle and vesicles aggregates can be loaded with a variety of different drugs or agents. Vesicles can also be loaded with magnetic particles, or can be complexed with proteins and DNA.

The greatest benefit to this process of production of the encapsulated bilayer structure is the great flexibility it allows in optimizing bilayer composition, aggregate size, etc. Also, as many of the steps in the process are spontaneous self-assembly steps, they are especially simple and only involve mixing one or more solutions. As a result, these steps are quite efficient and easy to scale up for commercial production. The methods can be expanded to encapsulate not only vesicles, but also polymer structures, DNA complexes, and protein structures.

The following examples are presented to illustrate the present invention and to assist one of ordinary skill in making and using the same. The examples are not intended in any way to otherwise limit the scope of the invention.

EXAMPLE 1

Figure 2:
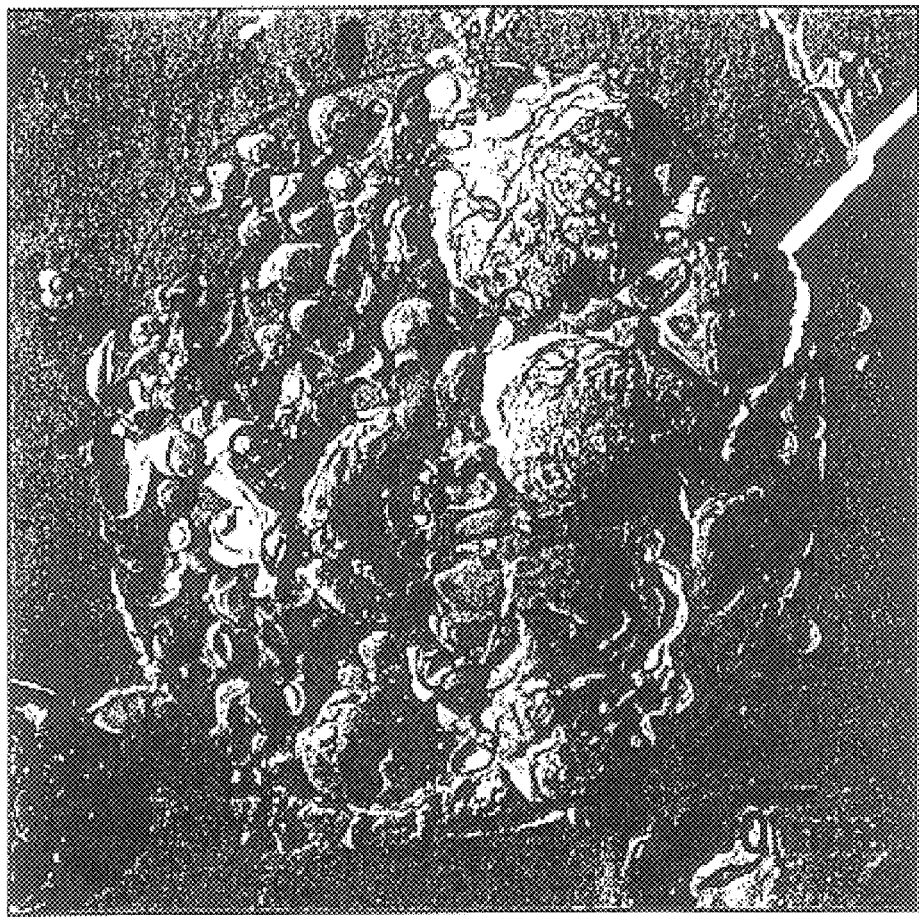
FIG. 2 is a freeze-fracture transmission electron micrograph of a typical vesosome of the invention prepared upon mixing cochleated cylinders with active sized aggregates (at a 1:1 mole ratio) after addition of EDTA. There was only one outer bilayer, and the interior vesicles appear to be specifically aggregated. The two figures differ only in that EDTA has been added to the second sample to chelate the remaining calcium.
Figure 3:
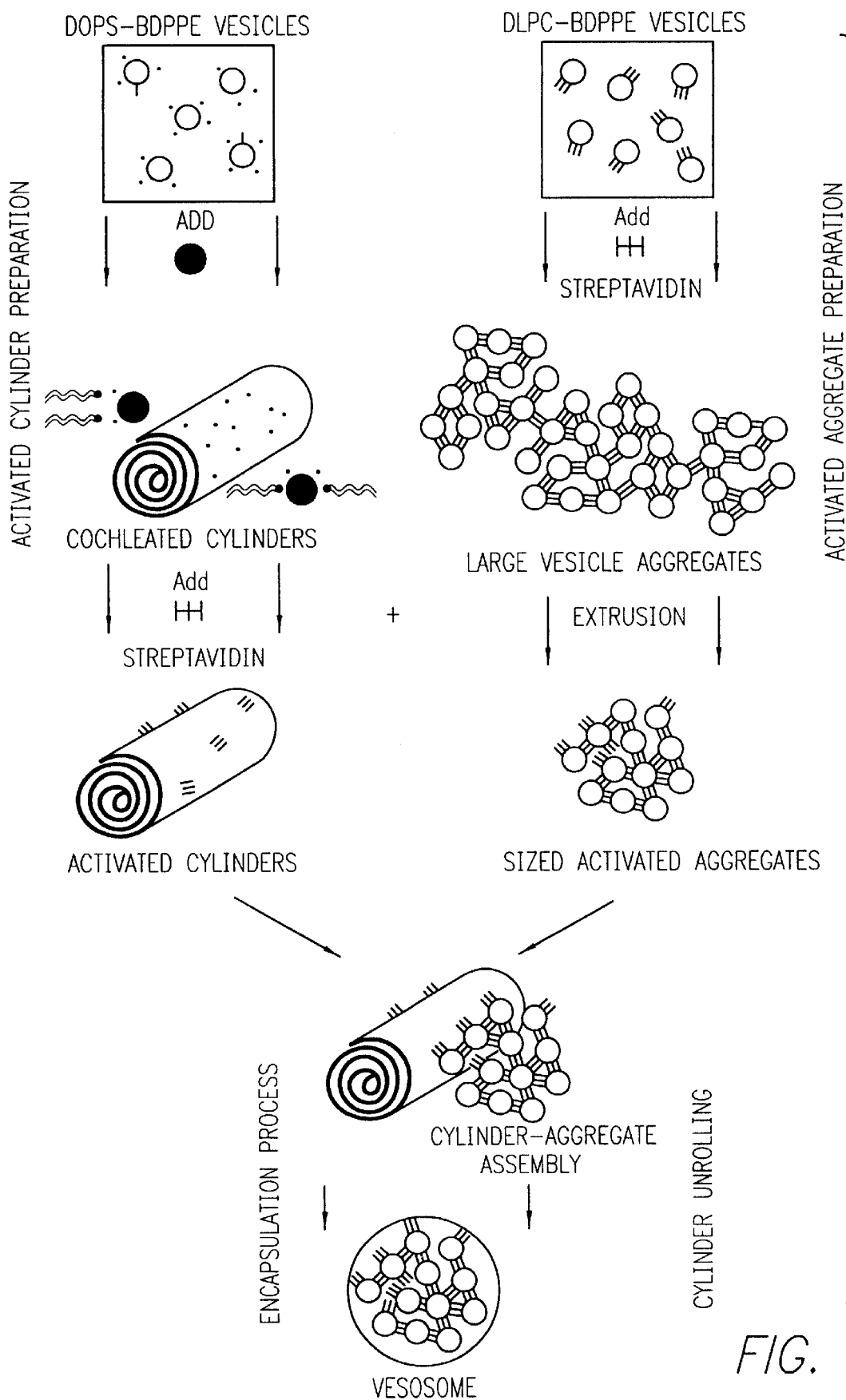
FIG. 3 is a schematic representation of one embodiment for vesosome production.

In this example, the preparation of a vesosome was essentially a two-step process (FIGS. 3 and 4). The first step was creating a controlled-size vesicle aggregate. The second step was encapsulating the vesicle aggregate within an outer bilayer membrane. Provided here is a specific example of the techniques used to create the vesosomes shown in FIGS. 1 and 2. In each case, the specifics of the lipids and crosslinking agents, the size distributions, etc., used are only representative, and can be optimized to suit the application.

Vesicle Preparation:

The vesicles can be made from a variety of phospholipids, cholesterol, fatty acids, etc. as needed. To create the vesosomes shown in FIGS. 1 and 2, 150 mg of dilauroylphosphatidylcholine (DLPC) (Avanti Polar Lipids, Alabaster, Ala.) and 0.4 mg of biotin-X-dipalmitoylphosphatidylethanolamine (B-DPPE) (Molecular Probes, Eugene, Oreg.) were mixed together in a 2-dram sample vial in chloroform (the B-DPPE was present at 0.163 mole % of total lipid in solution) to thoroughly mix the lipids. The chloroform was removed by evaporation under vacuum. 5 mL of aqueous buffer/salt/azide solution (100 mM NaCl, 50 mM TES, and 0.02 wt % $NaN_3$ balanced to pH 7.2) was added to the dried lipid to create a solution of 30 mg/mL total lipid. The sodium azide was used as a preservative, and is not necessary for the process.

After fully hydrating the lipids, the resultant solution consisted of multilamellar vesicles (MLVs). Unilamellar vesicles were formed from the MLV's by a mechanical extrusion technique [Mayer, E. (1985) *J. Microsc.* 140, 3–15]. The MLV solution was repeatedly (1) frozen in a liquid nitrogen (T=–190° C.) bath for 30–60 seconds, then (2) immediately melted in a 50–60° C. water bath. This process disrupted the multilamellar structure of the vesicles and lead to the formation of large unilamellar vesicles (LUVs; polydisperse, up to a few microns in size). The solution was then allowed to cool to room temperature (25° C.). The LUV suspension was then put through 8–12 high pressure (approximately 50 psi dry nitrogen) extrusion cycles by filtering the solution within an Extruder (Lipex Biomembranes, Vancouver, BC, Canada) through two stacked Nuclepore filters of pore diameter 0.1 $\mu$m. This process produced a 30 mg/mL monodisperse population of unilamellar vesicles (ULVs) approximately 100 nm in diameter. These vesicles consisted of DLPC and B-DPPE, with B-DPPE being present in the bilayer at 0.163 mole %. The biotin ligand was oriented away from the bilayer (in the same direction as the headgroups). This created a vesicle which has several ligands protruding from the both the interior and exterior surface. This solution of vesicles was then allowed to equilibrate for at least a few hours. Although metastable, these ULVs remain freely suspended for several weeks without reverting to their equilibrium MLV structure.

Vesicle Aggregate Preparation:

To aggregate the vesicles, an aqueous dispersion of streptavidin molecules (mol. wt. 60,000 g/mol) in the same buffer solution was added to the extruded vesicles. In this example, 3.94 mg of streptavidin (Molecular Probes, Eugene, Oreg.) was measured and mixed with 6.24 mL of the TES/NaCl/azide buffer solution to create a 0.63 mg/mL streptavidin solution. 1.0 mL of streptavidin solution was added to a vial containing 2.0 mL of the DLPC/B-DPPE ULV suspension. The overall biotin-streptavidin mole ratio for this system was about 15:1, however, the ratio of exposed biotin (biotins on the outer vesicle monolayer) to streptavidin was about 8:1. Since there were four identical binding sites of streptavidin available for binding, the ratio of exposed biotins to binding sites was 2:1. Within an hour, the 20 mg/mL ULV/streptavidin suspension changed color from clear and bluish to opaque and cloudy, indicating that much larger particles were being formed, i.e., the vesicles were aggregating. This vesicle aggregation scheme did not appear to stress or rupture the individual vesicles. [Chiruvolu, S., et al., (1994) *Science* 264, 1753–1756].

Controlled-size Vesicle Aggregates Preparation:

Preparation of uniform size of vesicle aggregate (i.e. vesicle aggregate sizing) was done by extruding the large vesicle aggregates through two stacked Nuclepore filters of pore diameter 1.0 $\mu$m; this extrusion was essentially identical to the extrusion step in ULV production, except the pore size was larger. This produced a dispersion of vesicle aggregates with sizes ranging from 0.3–1.0 $\mu$m. Once formed, the sized vesicle aggregates were stable for weeks and experience minimal re-aggregation or re-dispersion.

Encapsulating Sized Aggregates

To encapsulate the vesicle aggregate, advantage was taken of the microstructures common for negatively charged lipids in the presence of calcium ions. Cochleated cylinders are multilamellar lipid tubules formed spontaneously by certain negatively charged phospholipids in the presence of calcium ions. $Ca^{2+}$ is know to induce the adhesion, fusion and collapse of bilayers containing large proportions of the anionic phospholipid phosphatidylserine (PS) [Papahadjopoulos, D., et al., (1974) *Biochim. Biophys. Acta*, 401, 317–335; Papahadjopoulos, D., et al., (1975) *Biochim. Biophys. Acta*, 394, 483–491; Papahadjopoulos, D., et al., (1976) *Biochim. Biophys. Acta*, 448, 265–283]. These dehydrated multilamellar structures have been synthesized in the laboratory using similar techniques reported in the literature. The presence of cochleated cylinders was independently confirmed in the experiments by FF-TEM.

DOPS Unilamellar Vesicle Preparation:

Vesicles composed of 1,2 dioleoylphosphatidylserine (DOPS; AVANTI Polar Lipids, Inc., Alabaster, Ala.) and containing small amounts of B-DPPE (Molecular Probes, Inc., Eugene, Oreg.) were made as precursors to cochleated cylinders through similar methods as described above.

Briefly, 50 mg of lyophilized DOPS (61.7 $\mu$moles) was dissolved in 5 mL of Chloroform with 0.1 mL of B-DPPE solution [$9.8\times10^{-8}$ mole B-DPPE] to give a mole fraction of B-DPPE of 0.0016. The chloroform was evaporated under dry nitrogen and the lipid vacuum dried to remove excess solvent. The dried, mixed lipids were then hydrated (or resuspended) in 5 mL aqueous buffer solution as described above, yielding a solution with DOPS (MW 810 g/mol) concentration of 10 mg/mL (12.3 mM) and a B-DPPE (MW 1019 g/mol) concentration of 0.02 mg/mL (0.02 mM).

After dispersing the lipid by vortexing, equilibration of the solution was allowed at 37° C. for 24 hours. The multilamellar vesicle solution was taken through several freeze-thaw cycles prior to sizing by high pressure extrusion through Nuclepore 0.1 $\mu$m polycarbonate membranes. The sized vesicles were allowed to equilibrate at 25° C. prior to the addition of $Ca^{2+}$.

$Ca^{2+}$ Solution Preparation:

Solutions containing millimolar quantities of free $Ca^{2+}$ were prepared using anhydrous $CaCl_2$ salt (Sigma Chemical Co., St. Louis, Mo.) and the standard buffer solution. Previous experiments revealed that the concentration of $Ca^{2+}$ in solution required to induce fusion between small unilamellar vesicles of DOPS was greater than 2.0 mM. A 6.0 mM $CaCl_2$ buffer solution was prepared for use in these experiments.

Cochleated Cylinders Preparation:

Equal 1 mL volumes of the DOPS/B-DPPE vesicle solution (10 mg/mL) and the 6 mM $CaCl_2$ buffer solution were measured using two 1000 $\mu$L Hamilton Gas-Tight™ syringes. The two solutions were simultaneously dispensed into a clean, dry 3-dram vial. where they rapidly mixed to form a solution with a DOPS concentration of 5 mg/mL (6.2 mM), a B-DPPE concentration of 0.01 mg/mL (0.01 mM) and a $CaCl_2$ concentration of 3 mM. Immediately upon mixing, the turbidity of the solution increased. Aggregation, fusion and collapse of the DOPS/B-DPPE vesicles—and transition into cochleated cylinders—began immediately.

Streptavidin (Molecular Probes, Inc., Eugene Oreg.) was dissolved in the standard buffer for a solution with a concentration 0.63 mg/mL ($1.0\times10^{-8}$ mol/mL). 35 $\mu$L of the streptavidin solution was injected into 1 mL of the cochleated cylinder solution to activate the cylinders. The product was gently mixed and allowed to equilibrate for 24 hours.

Vesosome Preparation:

Provided above are descriptions of how to prepare the two precursor solutions (in identical buffers) needed for vesosome production. First, a solution of active vesicle aggregates (with some active freely floating vesicles) was prepared. Second, a solution of active cochleated cylinders (with likely some freely floating streptavidin) was made.

Two different mixing ratios were employed for the two precursor solutions that produce the vesosome solutions. To briefly describe, one mixture was prepared such that the ratio of the number of moles of DLPC lipids to DOPS lipids equaled one. The second mixture was prepared such that the ratio of the approximate number of sized vesicle aggregates (taking into account the freely floating vesicles) to the approximate number of cochleated cylinders equaled one. In the latter case, it was to attempted to match at least one aggregate with one cylinder. In the former case, it was to ensure that there were plenty of aggregates to get encapsulated.

In the mole-match case, 1.0 mL of the 5 mg/mL (DOPS) active cochleated cylinders/streptavidin solution was added to the 20 mg/mL (DLPC) 0.190 mL of active sized vesicle aggregates simultaneously. That is, 6.2 $\mu$mol of DOPS molecules were mixed with 6.2 $\mu$mol of DLPC molecules. Upon mixing, the solution turned from chunky, crystal-like structures consistent with suspensions of cylinder solutions to a more opaque and less chunky solution.

In the number-match case, 1.0 mL of the 5 mg/mL (DOPS) active cochleated cylinders/streptavidin solution was added to the 20 mg/mL (DLPC) 0.040 mL of active sized vesicle aggregates simultaneously. That is, 6.2 $\mu$mol of DOPS molecules was mixed with 1.3 $\mu$mol of DLPC molecules. Therefore, in the mole-match case, there were about 5 times as many aggregates as in the number-match case. Again, upon mixing, the nature of the solution changed.

Freeze-fracture TEM Results

Aliquots for freeze-fracture analysis were taken from both the mole-match and number-match solutions one day after mixing the cylinders and aggregates.

In general, FF-TEM revealed that most of the structures present in either the mole-matched or number-matched solution were LUVs (1–5 $\mu$m). Very few cylinders were observed. There did appear to be some unencapsulated sized aggregates, as well as, a high concentration of free vesicles (100 nm).

Several vesosomes were formed, as shown in FIG. 1. The interior aggregated vesicles: (1) appeared to resemble the aggregated vesicles in both size (~0.5 $\mu$m) and aggregation state (dense and compact) prior to mixing the solutions, and (2) were approximately 100 nm in size. These features indicated that the vesicles were indeed the DLPC vesicles and not DOPS vesicles, which remained even after $Ca^{2+}$ addition.

There were, however, a few larger vesicles present, and these may simply be larger DLPC ULVs or ULVs that had been formed by the fusion of several DLPC ULVs. The vesosome consisted of a single bilayer encapsulating the entire vesicle aggregate, consistent with the "unrolling" of a cylinder.

Although not wishing to be bound by any particular theory, the encapsulation of the vesicles could occur as follows: after mixing the solutions, an active aggregate approaches an active cylinder and binds to its surface by at least one biotin-streptavidin interaction. The aggregate proceeds to bind in several places until the binding force overcomes the force necessary to keep the cylinder wound. As the cylinder begins to unwind, the interior regions of the cylinder, now exposed to the aqueous solution, continue to bind around the aggregate until the cylinder unravels completely around the aggregate, as if "forced" by the presence of EDTA.

Next, 0.44 mL of 5 mM EDTA solution (in the same buffer) was added to 0.5 mL of the mole-matched cylinder-aggregate mixture. The cloudy, opaque solution immediately turned grayish and more transparent. This cylinder-aggregate mixture consisted of approximately 4.2 mg/mL DOPS (cylinders) and 3.2 mg/mL DLPC (aggregates). The amount of EDTA added was in excess of the amount necessary to completely bind all of the available calcium ions, and therefore, cause unraveling of the cylinders. Also, 0.5 mL of the 5 mM EDTA solution was added to the number-matched mixture. Again, the solution changed to grayish and transparent. This number-matched mixture consisted of 4.8 mg/mL DOPS and 0.8 mg/mL DLPC. Again, excess EDTA was added. Aliquots of each of these solutions, were also taken after approximately five hours of incubation, for freeze-fracture sample preparation.

FF-TEM again revealed that each of these solutions contained very many LUVs (1–5 $\mu$m), as is expected in solutions in which EDTA has been added to cylinders. Also, there were several ULVs but no cylinders.

Vesosomes again were present in the number-match solution. FIG. 2 shows a typical vesosome observed in these solutions. Note, again, that interior vesicles appeared to be aggregated as in the precursor solutions. However, there were also some very large vesicles, probably unraveled DOPS vesicles, which have become encapsulated as well. The number of vesosomes relative to the number of LUVs in these solutions did not seem to vary between the pre- and post-EDTA solutions, however, there seems to be more of them in the mole-matched solutions. This may indicate that the more active particles added to solution increase the chances for a vesosome to form.

It should be noted that the vesosome structures were not present in either of the precursor solutions. The solutions of cylinders saturated with streptavidin did not show any unusual characteristics due to the presence of the streptavidin; in fact, the cylinders seemed to become more dispersed, which may have been due to the bound streptavidin acting like a steric stabilizer, keeping the cylinders isolated from each other. The solutions of sized vesicles also did not exhibit any feature resembling a vesosome. No LUVs were even present in these solutions.

EXAMPLE 2

This example demonstrates the method of sizing of aggregated vesicles. A simple, one step process was developed to produce colloidal aggregates with a well defined size distribution, by controlling the ratio of reactive groups on the surface of the colloids (typically ligands such as a biotin coupled to a phospholipid incorporated in a vesicle membrane) to crosslinking agents (typically soluble biological receptors such as avidin or streptavidin) in solution. Other chemical ligands associated with the colloidal particles, and covalent crosslinking agents would also work as well. At a proscribed ratio of ligand to receptor, the receptor or crosslinker eventually saturates the ligands at the colloid surface, thereby limiting the aggregation process. This limited aggregation process was initiated by simple mixing of the ligand-labeled colloidal particles with the crosslinking agent or receptor. The crosslinking agent in solution competes for the limited number of surface ligands with ligands on other colloidal particles.

By having an excess of crosslinking agent, the ligands are eventually exhausted, and aggregation ceases when all of the ligands are coupled to a crosslinker. The process requires no specific mechanical or physical steps to initiate or limit the aggregation—aggregation proceeds by diffusion and reaction of the ligands and crosslinkers until equilibrium (at least metastable equilibrium) is reached. A mathematical model of the process was also developed that is consistent with experiment and shows a well defined transition between complete flocculation and limited aggregation that depends primarily on the ratio of crosslinker to surface ligands. This process can be generalized to any system of colloidal particles with surface accessible, reactive groups that can be coupled by a crosslinking agent.

The specific purpose of this embodiment is to have a one step method of producing vesicle aggregates of a limited size or aggregation number for use in making the vesosome drug delivery system (S. A. Walker et al., *Nature*, 387, 61–64 (1997)). Vesosomes comprise a sized aggregate of unilamellar vesicles attached to each other via ligand-receptor interactions, encapsulated in a second bilayer, also attached via ligand-receptor interactions (See FIG. 1). The interior vesicles can be of a uniform size and membrane or interior composition, or of varied sizes and/or membrane or interior composition. The exterior membrane may also be of different composition, and may incorporate specific recognition or steric stabilization molecules on the surface.

For example, the total dimensions (i.e. diameter) of a vesosome can be controlled from about 0.1 micron to >1 micron. The vesosome can incorporate a variety of water or lipid soluble drugs within the interior vesicles, or within the exterior capsule, or both. These drugs can then permeate slowly through the interior and exterior bilayers, providing a controlled, slow release of drugs over time.

The one step aggregation process replaces the more complex, multistep process that involves complete flocculation of the vesicles, followed by mechanical sizing via extrusion of the aggregated vesicles through filters of defined size (S. A. Walker et al., *Nature*, 387, 61–64 (1997)).

This process does not put any stress on the vesicles as they aggregate, nor does it require any additional filtering or purification steps, as in the previous process. The filtering process also results in debris from destroyed vesicles and aggregates that need to be removed prior to subsequent processing steps. Moreover, the surfaces of these limited aggregates are saturated by the crosslinking agent, hence the size distribution of the aggregates is stable for extended periods of time. The entire process is completed in a few minutes and requires no subsequent separations or purifications. The end result is a population of well-defined aggregates with surfaces saturated by streptavidin, avidin, or whatever crosslinking agent was used.

This process can be used much more generally to create a larger colloidal aggregate from small particles. The process is independent of the details of the colloidal particles, crosslinking agent, or surface associated ligand. Prior to this work, non-specific colloidal aggregation induced by attractive interactions between the particles could not typically be controlled, other than to completely inhibit aggregation by making the interaction between colloidal particles sufficiently repulsive. Once colloidal aggregation is initiated, the aggregates grow indefinitely and irreversibly. One of the only ways available to limit coagulation of liquid colloidal droplets is to use a surface-active compound that changes the interaction between the colloidal droplets as a function of surface coverage.

In what is generally referred to as limited coalescence, a fine emulsion of liquid droplets is generated whose surface area is much larger than can be completely covered by a surface stabilizing agent. These small droplets are unstable to coalescence and grow, with a concomitant reduction in total interfacial area, until the stabilizing agent covers the interface at a sufficient level to halt further coalescence (T. H. Whitesides and Ross *J. Colloid and Interface Science*, 169, 48–59 (1995)).

The ideal construction process for a sub-micron bilayer-based drug delivery system includes a series of equilibrium "self-assembly" steps that require only simple mixing and minimal equipment and minimal purification. The main benefit of this new embodiment is to increase the speed and efficiency of vesosome construction through (1) optimizing the vesicle aggregation process by creating a self-limiting, one-step aggregation process by controlling the ratio of streptavidin to biotin and the total vesicle concentration described by theoretical models of self-limiting vesicle aggregation. FIG. 1 shows an electron micrograph of a vesosome constructed of 0.1 micron diameter dilaurylphosphatidylcholine interior vesicles aggregated via biotinated lipids and streptavidin, encapsulated in a dioleoylphosphatidylserine bilayer, also coupled to the aggregate with the biotinated lipid—streptavidin linkage. The overall dimensions of the vesosome are about 0.5 microns. Increasing the efficiency of vesosome production is important for testing specific drug applications.

Vesosome Construction

The vesosome is designed to be sub-microscopic in size, with the interior vesicles ranging from, for example, 20–100 nm, and the entire aggregate from 0.1 to about 1 micron in diameter. FIG. 1 shows that the vesosome contains aggregated, spherical, unilamellar vesicles surrounded by an exterior membrane. The exterior membrane is continuous around the aggregated vesicles and the size distribution is consistent with that expected from the process described in this example.

The preparation of the vesosome was essentially a three-step process. The first step was making the interior vesicles and loading the specific drug to be delivered. These steps have been generally described in the literature (T. M. Allen et al., *Advanced Drug Delivery Reviews*, 16, 267–284 (1995); T. M. Allen, *Current Opinion in Colloid and Interface Science*, 1, 645–651 (1996); D. D. Lasic, *Liposomes: From Physics to Applications*, (Elsevier, Amsterdam (1993)); D. D. Lasic et al., *Current Opinion in Solid State and Materials Science*, 1, 392–400 (1996)). The second step was creating a controlled-size vesicle aggregate, without disrupting the vesicle bilayer or contents. The third step was encapsulating the vesicle aggregate within an outer membrane.

FIG. 4 shows the process for creating a controlled size vesicle aggregate in Example 1 and an additional embodiment of "self-limiting" aggregation in this Example. In the process of Example 1, biotin-labeled vesicles were added to streptavidin solution, leading to complete flocculation of the vesicles via biotin-streptavidin-biotin crosslinks. These flocculated vesicles were then reduced in size mechanically by extrusion through filters of a given pore size. This step was followed by purification of the extrudate to remove debris and disrupted vesicles.

In the process herein of Example 2, a controlled ratio of streptavidin or avidin was added to the biotin labeled vesicles (or any crosslinking agents), leading to aggregates of controlled size in a single mixing step. No mechanical sizing was needed. The process of Example 2 provides for the creation of aggregates that streamline vesosome production, eliminates time consuming mechanical filtration, separation, and extrusion steps, and helps to make the entire vesosome construction a simple series of controlled self-assemblies. These additional self-assembly tools of self-limiting aggregation should also have applications well beyond vesosome production, such as aggregation of colloidal particle.

Self-limiting Colloidal Aggregation Process

In the process of Example 1, as shown in FIG. 4, sufficient streptavidin (Molecular Probes, Eugene, Oreg.) in buffer was added to vesicles containing a small fraction of biotin-lipid (Biotin-X—DPPE, Molecular Probes) to produce an overall streptavidin to biotin-lipid ratio of 1:15; however, the ratio of streptavidin to biotin-lipid on the outside of the vesicle available for binding was approximately 1:8. The remainder of the vesicle bilayer composition could be varied between pure dioleoylphosphatidylcholine to mixtures of distearoylphosphatidylcholine and cholesterol and did not affect the results of the aggregation process. As streptavidin has four distinct binding sites for biotin, the ratio of streptavidin binding sites to exposed biotin was 1:2, meaning there were always unreacted biotin-lipids. Within an hour after adding the streptavidin to the vesicle solution, the suspension changed from clear and bluish to opaque and cloudy-white, indicating that vesicle aggregates were forming. Aggregation continued indefinitely, producing multi-micron sized aggregates that eventually flocculated (S. A. Walker et al., Nature, 387, 61–64 (1997); T. H. Whitesides et al., J. Colloid and Interface Science, 169, 48–59 (1995); S. Chiruvolu et al. Science, 264, 1753–1756 (1994)). However, aggregates for intravenous use must be of the order of 0.2–0.5 microns to facilitate long circulation times (with steric stabilization by PEG-lipid (T. M. Allen, Current Opinion in Colloid and Interface Science, 1, 645–651 (1996); D. D. Lasic, Liposomes: From Physics to Applications, (Elsevier, Amsterdam (1993); D. D. Lasic et al., Current Opinion in Solid State and Materials Science, 1, 392–400 (1996)). In the process of Example 1, the large vesicle aggregates were extruded through two stacked Nuclepore filters of pore size 1 μm. This produced a dispersion of vesicle aggregates with sizes ranging from 0.3–1.0 μm. The result that was that there was a large fraction of isolated vesicles and much smaller aggregates that would have to be removed at this step.

A simple, one-step, self-limiting aggregation process significantly increases both the efficiency and speed of vesosome construction. However, colloidal aggregation was typically an "all or nothing" process, when the interactions leading to the aggregation are attractive, but non-specific. However, it was found that if the ratio of streptavidin to biotin was increased so that there was roughly two biotin lipid sites available on the vesicle surface per streptavidin added (1:2) (experimentally, this corresponds to an initial mole ratio of roughly 4 biotin lipids per streptavidin, as half of the biotins point toward the interior of the vesicles, where they were not available for cross-linking), the aggregation process appears to be self-limiting. That is, the aggregation process stops with finite sized aggregates that are stable (See FIG. 5).

Modified Smolukowski Equation for Aggregation

In the original process described in Example 1 (S. A. Walker et al., Nature, 387, 61–64 (1997); T. H. Whitesides et al., J. Colloid and Interface Science, 169, 48–59 (1995); S. Chiruvolu et al., Science, 264, 1753–1756 (1994)), vesicles (0.1 micron diameter) incorporating a small fraction of biotin-lipid could be completely aggregated when sufficient streptavidin or avidin (Molecular Probes) was added to produce a streptavidin to exposed biotin-lipid mole ratio, R, of approximately 1:8.

Titration of vesicles incorporating 0.16 mol % of biotin-X DHPE with fluorescent BODIPY-labeled avidin or streptavidin (Molecular Probes, Eugene, Oreg.) showed that the fluorescence intensity increased linearly up to a streptavidin to total biotin-lipid mole ratio between 1:8 and 1:9, at which the fluorescence saturated. As streptavidin has 4 binding sites per molecule, this showed that roughly one half of the total biotin-lipids were exposed on the outside of the vesicle. This was consistent with the expected complete miscibility of the biotin-X DHPE with the vesicle phospholipids.

As streptavidin (or avidin) has four distinct binding sites for biotin, there were always unreacted biotin-lipids exposed on the vesicle surface. Within a few minutes after adding the streptavidin to the vesicle solution, the suspension changed from clear and bluish to opaque and cloudy-white, indicating that vesicle aggregates were forming. Aggregation continued indefinitely, producing multi-micron sized aggregates that flocculated 1 (S. A. Walker et al., Nature, 387, 61–64 (1997); S. Chiruvolu et al., Science, 264, 1753–1756 (1994)) (FIG. 6).

Figure 5:
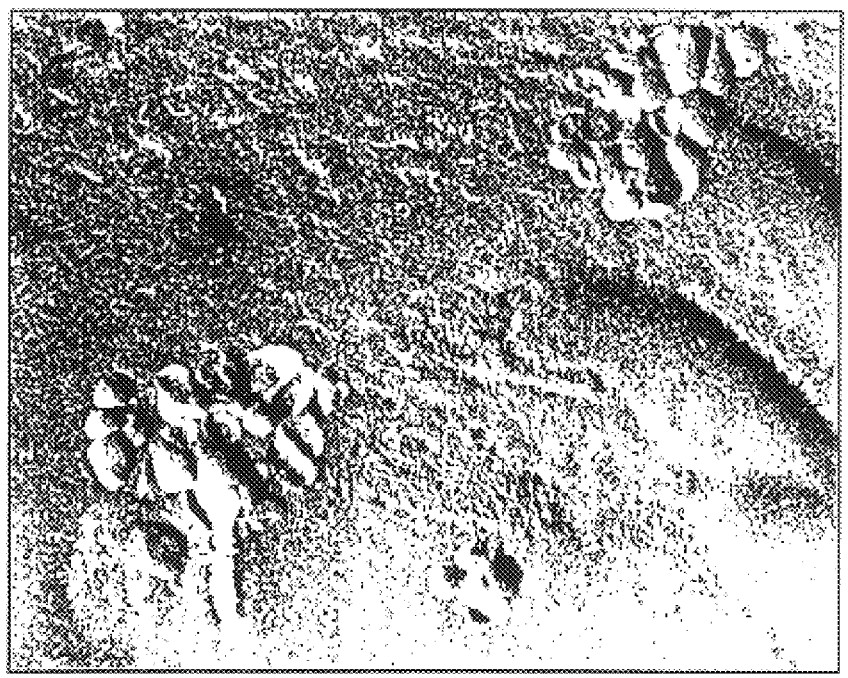
FIG. 5 is a photograph showing stable, small aggregates formed by adding streptavidin to biotin-labeled vesicles at a ratio of about 2 surface accessible biotins to streptavidin, corresponding to a total mole ratio of about 4 biotins per streptavidin, as described in Example 2, infra.
Figure 6:
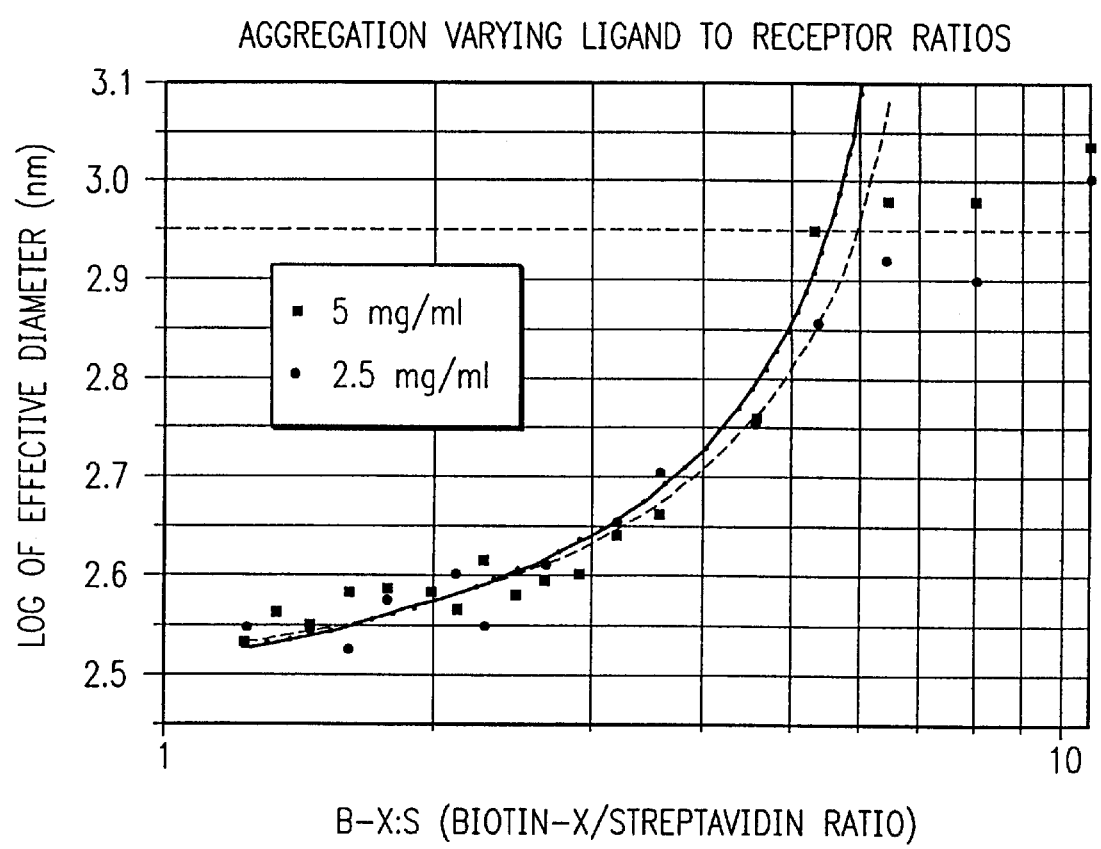
FIG. 6 is a line graph showing that vesicle aggregation and production continued indefinitely, producing multi-micron sized aggregates that flocculated, as described in Example 2, infra.

However, as the ratio, R, of streptavidin to exposed biotin-lipid was increased to one streptavidin to less than four biotin-lipids available on the vesicle surface ($R \leq 1:4$), aggregation began to diminish as shown by dynamic light (DLS) scattering (FIG. 6). As the streptavidin to exposed biotin-lipid ratio was further decreased, ($R \geq 1:2$) flocculation ceased and DLS showed a dramatic decrease in the average aggregate size. This was confirmed by freeze-fracture electron microscopy (J. A. Zasadzinski et al., J. Electron Microsc. Technique, 13, 309–334 (1989)) that showed a stable distribution of aggregates about 0.5 microns in diameter formed from the 0.1 micron diameter vesicles (FIG. 5). For larger values of R, the extent of aggregation did not change appreciably with R. No significant deformation of the vesicles occurred during any of the aggregation processes as shown by similar releases of entrapped carboxyfluorescein dye from aggregated and unaggregated vesicles (Kisak, E. et al., Langmuir, 2000, 16, 2825).

While previous experiments showed that excess biotin-lipid led to complete aggregation (S. A. Walker et al., Nature, 387, 61–64 (1997); T. H. Whitesides et al., J. Colloid and Interface Science, 169, 48–59 (1995); S. Chiruvolu et al., Science, 264, 1753–1756 (1994)), and a large excess of streptavidin led to very limited aggregation (H. C. Loughrey et al., Biochim. Biophys. Acta, 1028, 73–81 (1990)), the dramatic transition with receptor-ligand ratio was surprising. Vesicles aggregate by coupling a biotin-lipid on one vesicle to a streptavidin bound to a biotin-lipid on a second vesicle. The initial step in this process is the binding of a streptavidin in solution to the biotin lipid on a given vesicle. A competition for available biotin sites is set up between free streptavidin in solution and streptavidin already bound to another vesicle. Hence, the aggregation process is both initiated and inhibited by free receptor in solution. Sufficient streptavidin in solution eventually leads to the saturation of the ligands on the surface of the growing aggregate. Once all of the biotin-lipid sites on the growing vesicle aggregates are saturated with streptavidin, aggregation ends, leaving finite sized aggregates. The classical description of rapid aggregation of colloidal particles is given by the Smolukowski equation, which has been shown to give reasonable agreement with experiment for non-specific, diffusion-controlled colloidal aggregation (D. F. Evans et al., The Colloidal Domain, (VCH Publishers, New York, 1994)). The Smolukowski equation gives the diffusion controlled rate of production of aggregates of size j and concentration $[P_j]$ from smaller aggregates (i<j), less the consumption of aggregates of size j by further aggregation with any other aggregate. The rate constant, k is given by the mutual diffusion of the particles toward each other and is assumed to be constant, independent of the size of the particles or the aggregates:

$$d[P_j]/dt = k\left[1/2\sum_{i>j}[P_i][P_{j-i}], -[P_j]\sum_i[P_i]\right] \quad (1)$$

and the change in the total particle concentration, $$\sum_i [P_j]$$

is:

$$d/dt \sum_j [P_j] = -k/2\left(\sum_j [P_j]\right)^2 \quad (2)$$

For an initial monomer (vesicle) concentration, $[P_o]$, at t=0, Eqn. 3 has the solution:

$$\sum_j [P_j] = [P_0]/1 + t/\tau \quad (3)$$

in which $\tau = 2/k[P_o]$. The mean aggregation number, M, diverges for long times, resulting in flocculation of the colloidal particles:

$$M = [P_0]/\sum_j [P_j] = 1 + t/\tau \quad (4)$$

The diffusion limited rate constant, $k_{ij}$, is given by the mutual diffusion of the particles toward each other: $k_{ij} = 2k_BT/3\eta(1/R_i+1/R_J)(R_i+R_J)$. For the limiting case of $R_i=R_j$, $k_{ij}=k=8k_BT/3\eta=8\times10^9$ liter/mol-sec, in which $k_B$ is Boltzman's constant, T is absolute temperature, and $\eta$ is the solvent viscosity. For ligand-receptor induced aggregation, a much lower rate constant than diffusion limited is expected due to the steric requirements of the ligand-receptor bond.

Self-Limiting Aggregation

However, these expressions do not describe aggregation caused by cross-linking a limited number of reactive sites on the colloid surfaces. Biotin-lipids on different vesicles must be crosslinked by streptavidin to induce aggregation. If $\theta$ is the average fraction of biotin-lipids bound to streptavidin, a vesicle with $\theta>0$ must contact a vesicle with free biotin-lipid, $(1-\theta)>0$, in order for the vesicles to bind. The new expression for the change of total particle concentration is (See Eqns.3,4):

$$d/dt \sum_j [P_j] = -k/2(\theta(1-\theta))\left(\sum_j [P_j]\right)^2 \quad (5)$$

As $\theta$ goes from zero to one, the rate of aggregation goes through a maximum, then decreases and eventually stops, giving a finite number of aggregates:

$$\sum_j [P_j] = [P_0]/1 + \left[\left(\int_0^t \theta(1-\theta)dt\right)/\tau\right] \quad (6)$$

with a finite aggregate size, M:

$$M = 1 + \left[\left(\int_0^\infty \theta(1-\theta)dt\right)/\tau\right] \quad (7)$$

again, $\tau=2/k[P_o]$. The average particle size depends on the time evolution of the bound biotin fraction, $\theta$, which in turn is coupled to the size distribution, $[P_j]$.

However, it is possible to write a simplified equation for $\theta$ that reflects the initial competition for biotin sites on the unaggregated vesicles, and thereby decouple the expressions for $[P_j]$ and $\theta$. The first term in Eqn. 8 is a simple binary expression for reaction of the biotin sites with streptavidin in solution.

The second term on the right hand side of Equation 8 is the crosslinking of a streptavidin occupied site on one vesicle with a free biotin site on a second vesicle:

$$n[P_0]\frac{d\theta}{dt} = k_1 n[P_o](1-\theta)N_s + k_2(n[P_o])^2\theta(1-\theta) \quad (8)$$

n is the number of exposed biotin sites per vesicle; the vesicles are at an initial concentration of $[P_o]$. Hence, $n[P_o]$ is the total biotin-lipid concentration exposed on the surface of the vesicles.

Titration of vesicles incorporating 0.16 mol % of biotin-X DHPE with fluorescent BODIPY-labeled avidin or streptavidin (Molecular Probes, Eugene, Oreg.) showed that the fluorescence intensity increased linearly up to a streptavidin to total biotin-lipid mole ratio between 1:8 and 1:9 at which the fluorescence saturated. As streptavidin has 4 binding sites per molecule, this shows that roughly one half of the total biotin-lipids were exposed on the outside of the vesicle. This is consistent with the expected complete miscibility of the biotin-X DHPE with the vesicle phospholipids.

$N_s$ is the concentration of streptavidin in solution:

$$N_s = N_{s,o} - \beta n[P_o]\theta \quad (9)$$

$N_{s,o}$ is the initial streptavidin concentration and $\beta$ is ratio of streptavidin to bound biotin. $\beta$ varies from 1, which corresponds to only one of the binding sites of streptavidin being full, to ¼, which corresponds to all four streptavidin sites being bound to biotin: $\frac{1}{4} \leq \beta \leq 1$. To decouple the equations, it is necessary to make $\beta$ constant.

$\beta$ must start out equal to 1, then decrease to a lower value that likely depends on the streptavidin to biotin ratio. However, good agreement with the fluorescence data. (FIG. 5) is obtained with $\delta$ treated as a fitting parameter, suggesting that $\beta$ approaches a steady state value.

Inserting Eqn. 9 into Eqn. 8, we have, with $R=N_{s,o}/n[P_o]$ as the initial ratio of streptavidin to exposed biotin-lipids:

$$\frac{d\theta}{dt} = n[P_0]k_1(R - \delta\theta)(1-\theta) \quad (10)$$

$$\delta = \beta - \frac{k_2}{k_1}$$

The solution for θ has the following form:

$$\theta = \frac{\exp\left[\left(1-\frac{\delta}{R}\right)\frac{t}{\tau_1}\right]-1}{\exp\left[\left(1-\frac{\delta}{R}\right)\frac{t}{\tau_1}\right]-\frac{\delta}{R}} \quad (11)$$

$\tau_1 = 1/k_1 N_{s,o}$, the time constant for streptavidin addition to biotin-lipids. For $\delta/R<1$, for long times (t->∞), θ->1 and the outer vesicle surface is saturated by streptavidin. For $\delta/R>1$, θ->R/δ, and there are always unreacted biotin-lipids on the vesicle surface. Inserting Eqn. 11 into Eqn. 7, for $\delta/R<1$, gives the mean aggregate size at equilibrium:

$$M = 1 + \frac{\tau_1}{\tau}\left(\frac{R}{\delta}\right)^2\left[-\left(\frac{\delta}{R}\right)-\ln\left(1-\frac{\delta}{R}\right)\right] \quad (12)$$

M diverges for $\delta/R \geq 1$. Eqn 12 gives a very good representation of the DLS data in FIG. 6. From FIG. 6, the extent of aggregation is independent of vesicle and streptavidin concentration, and the critical value of R when the aggregate size diverges (corresponding to $\delta/R=1$ in Eqn. 12), is $R_{crit} \approx 0.3 = \delta_{crit}$.

Diffusion and reaction of biotin-lipid with a biotin-lipid attached to streptavidin on a given vesicle also leads to an increase in θ. Biotin-lipid and/or biotin-lipid attached to a streptavidin will also diffuse towards existing contact sites between vesicles. At these contact sites, multiple bonds between a vesicle pair can form, leading to a depletion of free biotin (D. Leckband et al., Nature, 376, 617–618 (1995)). In Eqn. 8, these effects have the same form as the second term of Eqn. 8, with $k_2$ being replaced by an effective rate constant that reflects all three possible effects. As $k_2$ increases relative to $k_1$, δ decreases relative to R (Eqn. 10), and θ->1 faster (Eqn. 11). If the vesicle suspension is sufficiently dilute, complete aggregation does not occur for any value of R, and there is no threshold. For these experiments, this occurred for vesicle concentrations ≦1 mg/ml (D. A. Noppl-Simson et al., Biophysical Journal, 70, 1391–1401 (1996)).

The model can be further evaluated by monitoring the time dependence of the fluorescence of BODIPY-labeled streptavidin as it binds to the biotin-lipids. The fluorescence of the labeled streptavidin is linearly proportional to the number of biotins bound to the streptavidin; hence, this is a direct measure of θ, the average fraction of bound biotin-lipids (N. Emans et al., Biophysical Journal, 69, 716–728 (1995)). The fluorescence intensity as a function of time was measured for a fixed BODIPY-labeled streptavidin concentration ($N_{s,o}$ constant in Eqns. 10–12) when different concentrations of 0.1 micron vesicles of DLPC vesicles incorporating 0.16 mole % of biotin-X DHPC were added and allowed to aggregate. The fit of this data to Eqn. 12 for all of the ratios was surprisingly good considering the limitation of the model. Averaging from the fits, $\tau_1 = 1/k_1 N_{s,o}$, which should be constant between the experiments, is ≈700±100 sec; hence $k_1 \approx 4 \times 10^4$ liter/mol-sec. The diffusion limited rate constant, $k_{ij}$, is given by the mutual diffusion of the particles toward each other: $k_{ij} = 2k_B T/3\eta(1/R_i + 1/R_j)(R_i + R_j)$. For the limiting case of $R_i = R_j$, $k_{ij} = k = 8k_B T/3\eta = 8 \times 10^9$ liter/mol-sec, in which $k_B$ is Boltzman's constant, T is absolute temperature, and η is the solvent viscosity. For ligand-receptor induced aggregation, a much lower rate constant than diffusion limited is expected due to the steric requirements of the ligand-receptor bond (Kisak, E. et al., Langmuir, 2000, 16, 2825).

The second parameter, δ, increases as R increases, from about 0.2 at R=0.125 to about 0.3 for R=0.5 to nearly 1 when R=4, but more slowly than R, leading to the crossover between complete flocculation ($\delta/R>1$) to self-limited aggregation ($\delta/R<1$). The increasing value of δ suggests that that the average number of streptavidins per bound biotin-lipids, β, in Eqn. 11, increases as R increases, which is consistent with saturation of the vesicle surfaces with streptavidin. The competition for the biotin-lipids at the vesicle surface appears to be the cause of the percolation-like behavior.

To summarize, the extent of ligand-receptor induced vesicle aggregation can be controlled by varying the ratio of soluble receptor to surface-bound ligands. Aggregation exhibits a dramatic change with this ratio—below a critical value, aggregation is self-limiting, the aggregation numbers are finite, and the aggregates remain suspended in solution. Above this critical value, aggregation is complete and the aggregates grow indefinitely and flocculate. A biological system could be controlled to exist near this percolation threshold so that only small perturbations would cause the system to cross-over. The threshold could also be crossed by altering the number of binding sites on the receptor, or by altering the long-range forces between the ligands and receptors (D. Leckband, Nature, 376, 617–618 (1995); D. E. Leckband et al., Biochemistry, 33, 4611–4624 (1994); D. Leckband et al., Biophys. J., 69, 1162–1169 (1995)), between the receptors and vesicles, or between the vesicles themselves (S. A. Walker et al., Langmuir, 13, 5076–5081 (1997)). This type of reaction-induced aggregation can also be generalized to other colloidal systems by incorporating a competitive cross-linking reaction at the colloid surface and would be a useful new way to controllably alter the size distribution of a colloidal dispersion.

EXAMPLE 3

In this embodiment new vesosomes were prepared by a three-stage process that primarily differs from the previous process (described in Example 1) in the encapsulation step [S. A. Walker, et al., Nature 387, 61 (1997)].

In the first stage, the vesicles were prepared that were to be encapsulated. These encapsulated vesicles are loaded with the desired drug compound, or contain the drug within the lipid bilayer. Any number of different procedures known in the art can be used to prepare the encapsulated vesicles: sonication, extrusion, dialysis, etc. The encapsulation process is generally insensitive to the choice of encapsulated vesicles, so a wide variety of different lipid compositions can be chosen.

Vesicle Preparation:

Standard vesicles were composed of DSPC (1,2 Distearoyl-sn-Glycerol-Phosphocholine)/Chol (cholesterol) mixed at a 2:1 molar ratio. They were formed by first mixing the lipids in chloroform at the desired molar ratio. The chloroform was removed by blowing dry nitrogen on the solution, and then evaporating the residual chloroform under vacuum. The dried lipid film was then hydrated with buffer (100 mM NaCl, 50 mM TES, and 0.02 wt % $NaN_3$ balanced at pH 7.4) while maintained at approximately 55° C. The sodium azide is a preservative, and was not necessary for the process. Hydrating the lipid film caused the formation of multilamellar vesicles (MLVs).

The solution of MLVs was then put through a series of 8 freeze-thaw cycles which consist of (1) freezing the solution in a liquid nitrogen bath (T=−190° C.), then (2) immediately melting the solution in a water bath heated to 50–60° C. This process disrupted the multilamellar structure causing the formation of large unilamellar vesicles (LUVs) which were polydisperse in size. The solution was then heated to 55° C., and put through a series of 8–12 high pressure (approximately 50 psi dry nitrogen) extrusion cycles by filtering the solution with an Extruder (Lipex Biomembranes, Vancouver, BC, Canada) through two stacked Nucleopore filters of pore size 0.05 μm. This process produced a solution of monodisperse vesicles, which were between 50–70 nm in diameter. Other vesicles of differing lipid compositions, such as, DPPC/cholesterol, egg lecithin/cholesterol, DLPC, soy lecithin and DPPG/DPPC, can be employed.

Vesicle Aggregate Preparation:

Encapsulated vesicle aggregates were formed by first making a stock solution of 50 nm DSPC/Chol (2:1 molar ratio) vesicles which had been loaded with 0.16 mol % Biotin-X/DPPE(N-((6-(biotinoyl)amino)hexanoyl)-1,2-Dipalmitoyl-sn-Glycerol Phosphoethanolamine). The vesicles were formed following the same procedure outlined above in this example. These vesicles were then aggregated by adding avidin, which had been dispersed in the same buffer solution as above.

Two types of vesicle aggregates were made: massive aggregates and "quenched" aggregates [E. Kisak, et al. *Langmuir* 16, 2825 (2000)]. Massive aggregates were formed by adding avidin to the biotinylated vesicles at a 3:32 avidin to biotin molar ratio. These aggregates were multi-micron in size and loosely packed. Quenched aggregates were formed by adding avidin to the biotinylated vesicles at a 3:4 avidin to biotin molar ratio. These aggregates were compact and typically consisted of 8–12 vesicles tightly bound together. This method of vesicle aggregation does not rupture the individual vesicles or lead to loss of the interior contents.

Interdigitated Bilayer Sheet Preparation

The second stage of the vesosome production was preparation of the encapsulating bilayer. This bilayer forms the outer shell of the vesosome. Encapsulating bilayers were prepared by first making interdigitated bilayer sheets by adding ethanol to a vesicle solution. It has been shown [L. T. Boni, et al. *Biochimica et Biophyisca Acta* 1146, 247 (1993)] that if the vesicles are small enough, the added ethanol will cause the vesicles to fuse and form large bilayer sheets. When the sheets are heated past the gel state to liquid crystalline, or melting temperature, $T_c$, of the lipid bilayer, (about 41 C for DPPC bilayers) they roll up to form IFVs (interdigitated fusion vesicles), which are usually unilamellar and on the order of 0.5–2 μm in size [P. L. Ahl, et al. *Biochimica et Biophysica Acta* 1195, 237 (1994)] (FIG. 13B).

In this case, the interdigitated sheets that were used were made of 50 nm DPPC, or 50 nm DPPC/Chol 97.5:2.5 (molar ratio) vesicles. These vesicles were prepared by the extrusion procedure outlined above in this example. The vesicles were fused by adding enough ethanol to provide a final concentration of 3M ethanol (at 3M EtOH, fusion is complete and IFVs that form are smooth and spherical in nature). The ethanol was added dropwise while the solution was stirred. The newly formed sheets were diluted with an excess of buffer and centrifuged to the bottom of the vessel in order to wash away excess ethanol. The clear supernatant was then removed, and the washing procedure was repeated. The residual ethanol was no more than 0.1 M. The interdigitated lipid sheet flocculate was stable against transformation to closed vesicles even after the ethanol was removed, as long as the sheet solution was held below $T_c$. The washed sheets were then diluted to the desired concentration by adding buffer (it was assumed that no lipid sheets are lost in the supernatant that is removed). The interdigitated sheets remained stable throughout the washing procedure.

Encapsulating Sized Aggregates

A solution of free or aggregated lipid vesicles was mixed with a solution of washed interdigitated sheets. A colloidal solution or biological macromolecules could be encapsulated instead of vesicles. The mixture was briefly vortexed and then heated in a water bath at a temperature above the $T_c$ of the interdigitated sheets for 20 minutes. Typical sheets were made of DPPC ($T_c$~41° C.) and in this case the solution was heated at 46° C. Heating the mixture above $T_c$ caused the sheets to roll up and form mostly unilamellar IFVs, encapsulating vesicles or vesicle aggregates in the process.

Vesosomes Containing Quenched Aggregates and a Biotin-Containing Outer Bilayer

Figure 7:
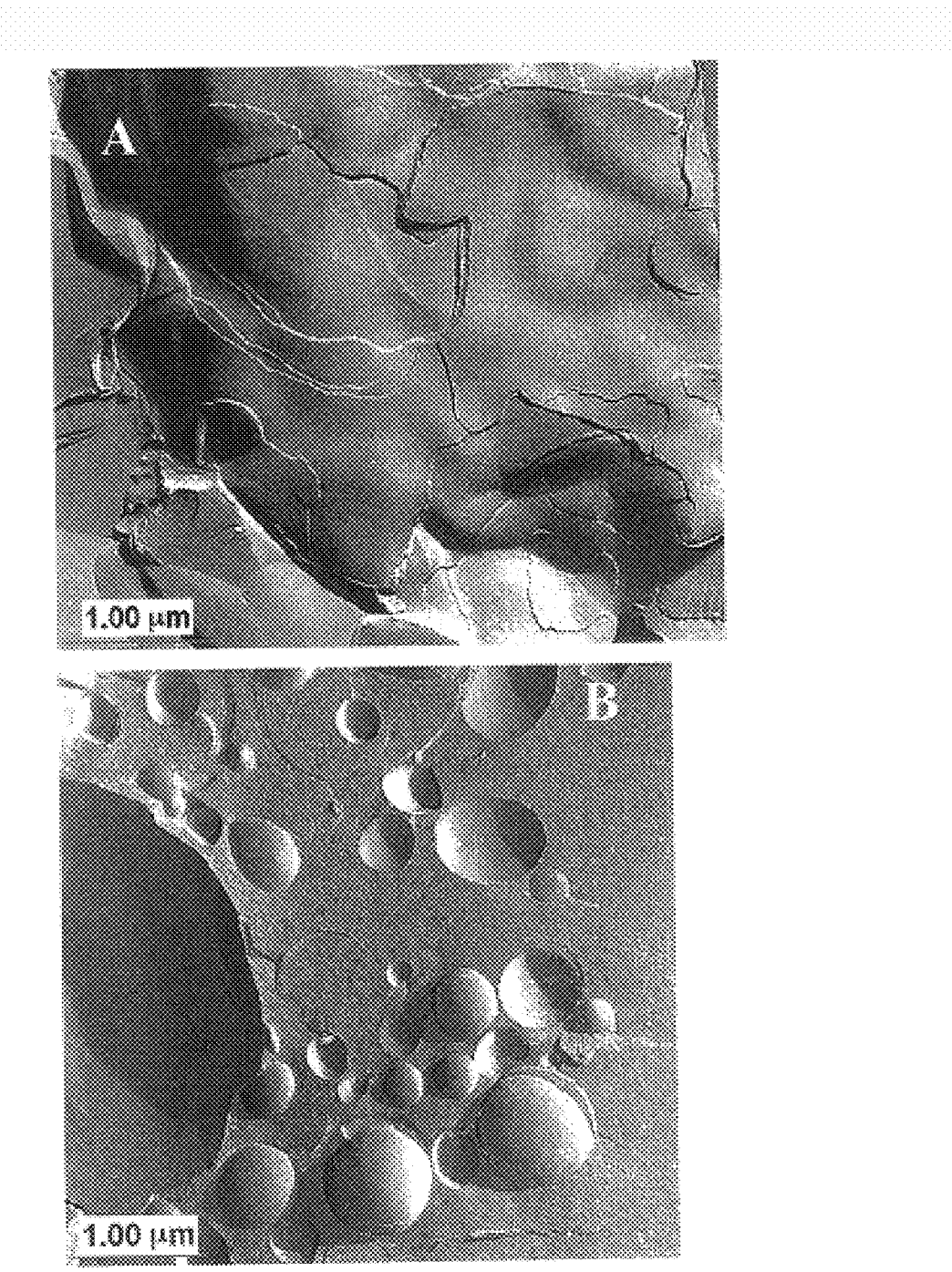
FIGS. 7A and B depicts (A) A typical freeze-fracture TEM picture of interdigitated sheets that form when small lipid vesicles were fused using ethanol, in this case 50 nm DPPC vesicles were fused with 3M EtOH, as described in Example 3, infra. (B) Typical image of vesicles that form after interdigitated sheets were heated past their $T_C$. In this case, the DPPC 3M EtOH sheets were heated to 46° C. for twenty minutes to form the vesicles.
Figure 8:
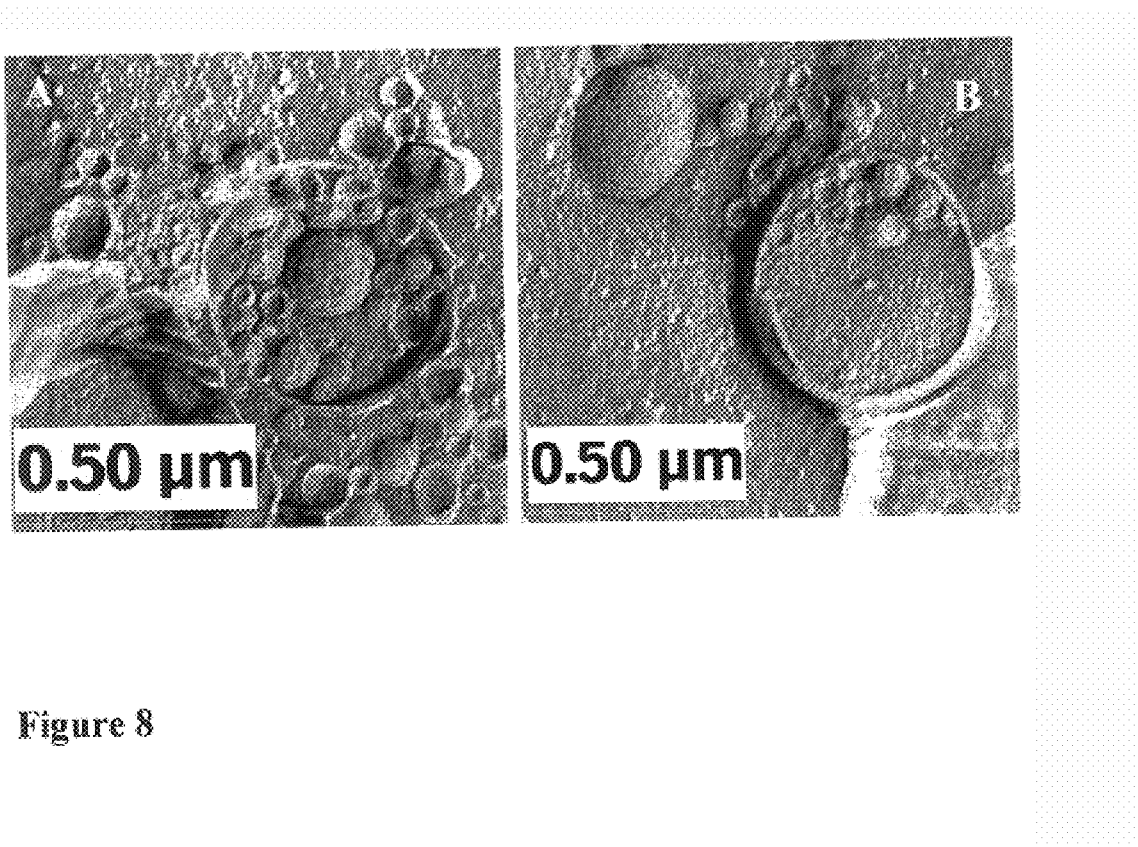
FIGS. 8A and B is a (A) freeze-fracture TEM picture of a vesosome produced by crosslinking sized aggregate vesicles with biotin loaded interdigitated sheets, as described in Example 3, infra. (B) Another vesosome formed with sized aggregates and biotin loaded sheets.

In one variation of the vesosome production, a biotin/avidin ligand-receptor system was used. The outer encapsulating bilayer was produced by making 50 nm DPPC vesicles loaded with 1 mol % Biotin-X/DPPE, which were then fused using enough ethanol to make a 3M EtOH solution. A typical TEM image of these interdigitated sheets is shown in FIG. 7. These bilayer sheets were stable even after the excess ethanol was removed from solution. The structures range in size from 0.25 to 3 microns and were usually unilamellar. Sized aggregates can be seen bound to both the outside and inside of the IFV surface as shown in FIG. 8. A 0.5 ml aliquot of a 50 nm DPPC vesicle solution at a concentration of 25 mg/ml was fused by drop-wise adding 0.106 ml of ethanol while the solution was being stirred. The sheets were then washed by diluting the solution with 5 ml buffer, centrifuging, and removing supernatant. This was done twice. The washed sheets were then diluted to 25 mg/ml by adding buffer.

A batch of 50 nm DSPC/Chol (2:1) vesicles loaded with 0.16 mol % Biotin-X/DPPE was produced at a concentration of 25 mg/ml. These vesicles were aggregated to form quenched aggregates of roughly 10 vesicles each by adding avidin at a 3:4 avidin to biotin ratio [E. Kisak, et al. *Langmuir* 16, 2825 (2000)]. As shown in FIG. 8, a 0.2 ml aliquot of the 25 mg/ml vesicles solution was added to 0.56 ml of buffer, and then aggregated by adding 0.24 ml of the avidin solution (avidin was dissolved in buffer at a concentration of 2.5 mg/ml). The final concentration of the aggregates was 5 mg/ml. The quenched aggregates that were formed have their surfaces saturated with avidins, allowing for further crosslinking.

In order to encapsulate the vesicles, a 0.5 ml aliquot of the 25 mg lipid/ml washed interdigitated DPPC/(Biotin-X/DPPE) sheets was added to 0.5 ml of the 5 mg lipid/ml quenched DSPC/Chol aggregates. The solution was briefly vortexed and allowed to sit overnight to allow crosslinking to occur between the sheets and aggregates. Finally, the mixture was heated to 46° C. in a water bath for 20 minutes. A typical result is shown in FIG. 8. Encapsulation was successful with a number of aggregates enclosed in a second, continuous outer bilayer membrane. The aggregates remained quenched, and aggregate to IFV binding was evident. Since Biotin-X/DPPE was present on both bilayer surfaces, crosslinking can occur on either side. As can be seen in FIG. 8B, an aggregate was bound to the bilayer surface and was encapsulated as the bilayer peeled up to form an IFV. Another aggregate was shown to be either originally crosslinked to the other side of the sheet, or crosslinked to the IFV, after it formed. Sheets loaded with 0.3–3 mol % Biotin-X, comprised of either DPPC or 70:30 DPPC/DHPC mixtures, were crosslinked with aggregates at different sheet to aggregate weight ratios.

Vesosomes Containing Massive Aggregates and Outer Bilayer Without Biotin

Figure 9:
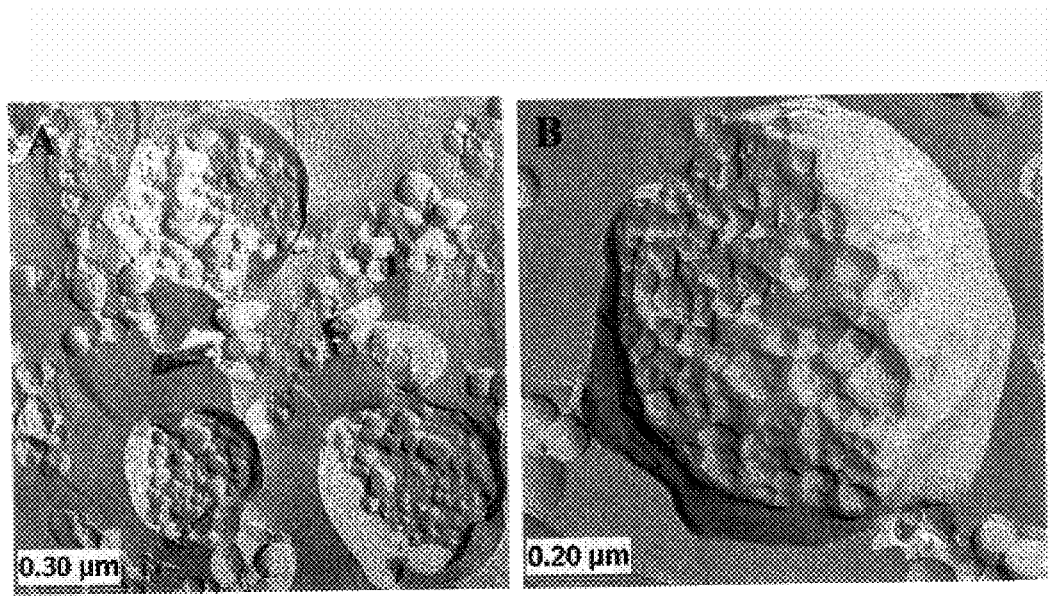
FIG. 9 illustrates (A) a TEM image of multiple vesosomes that have formed after adding massive aggregates to interdigitated sheets of pure DPPC, as described in Example 3, infra. Excess aggregates can be seen in solution. No specific binding is present between aggregates and outer membranes. (B) a close-up of a massive aggregate encapsulated vesosome. Encapsulated vesicles have retained their size (~50–70 nm).

A second variation of using interdigitated sheets for encapsulation did not rely on biotin/avidin crosslinking of the aggregates to the sheets (FIG. 9). This may be a superior method in practice, as (1) an immune system response to the biotin, avidin, or streptavidin is avoided due to the absence of crosslinking proteins in the outer encapsulating bilayer, (2) the costs of biotin and avidin are reduced, and (3) one of the aggregation steps is eliminated. In this case, pure washed DPPC sheets were used (no Biotin-X/DPPE was added). The sheets were made by fusing 0.5 ml of 50 nm DPPC vesicles (concentration 50 mg/ml) with 0.106 ml of ethanol. The sheets were washed as above and diluted to a final concentration of 50 mg/ml.

Next, a solution of vesicle aggregates was prepared, but in this variation of the process, massive aggregates instead of quenched aggregates were used. The massive aggregates were formed by adding 0.24 ml avidin solution (2.5 mg/ml) with 0.36 ml buffer and then adding this mixture to a 0.4 ml aliquot of 50 nm DSPC/Chol (2:1) vesicles (concentration 100 mg/ml) loaded with 0.16 mol % Biotin-X/DPPE. The final molar ratio of avidin to biotin was 3:32.

The vesicles rapidly aggregated and completely flocculated to the vessel bottom, leaving a clear supernatant (Chirovolu, et. al., *Science*, 1994, 264, 763). The aggregates were briefly centrifuged and the supernatant removed, leaving a 0.4 ml solution of massive aggregates at a concentration of approximately 100 mg/ml. The aggregate solution was then mixed with the above DPPC solution (no Biotin-X) by adding a 0.35 ml aliquot of vesicle aggregates to a 0.1 ml aliquot of the DPPC sheets. The mixture was then briefly vortexed and heated in a water bath at 46° C. for 20 minutes. The resultant IFVs structures were imaged via freeze-fracture TEM. As indicated by FIG. 9, large numbers of vesicle aggregates were encapsulated. These vesosomes varied in size from 0.5–2 $\mu$m, were tightly packed and were predominantly unilamellar in nature (although some multilamellar shells were observed). The interior vesicles retained their size and remained as distinct vesicles, without any shared bilayer walls.

Vesosomes Containing Free Aggregates and Biotin Free Outer Bilayer

Figure 10:
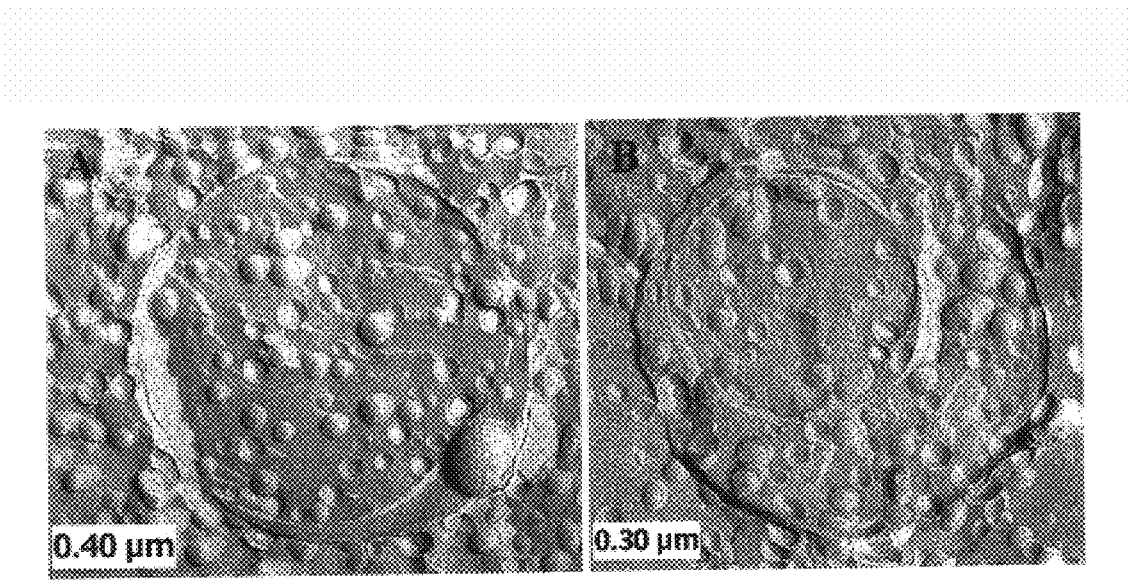
FIG. 10 shows a vesosome formed by adding a dense population of 50 nm DSPC/Chol vesicles to DPPC interdigitated sheets, as described in Example 3, infra. The populations of vesicles inside and outside of the shell, formed from the interdigitated sheets, are equivalent.

The third variation of vesicle encapsulation within an outer bilayer simply employed free vesicles, not aggregates. No crosslinking molecules were employed anywhere in the process. In this case DPPC sheets were again prepared by mixing a 0.5 ml aliquot of 50 nm DPPC vesicles (concentration 50 mg/ml) with 0.106 ml of ethanol (finally molarity is 3M ethanol). The sheets were washed and diluted to a final concentration of 50 mg/ml. Next, a 50 nm DSPC/Chol (2:1) vesicle solution (no added biotin lipids) was prepared at a much higher concentration of 200 mg/ml by the usual extrusion methodology. A mixture of the DPPC sheets and DSPC/Chol vesicles was prepared by using a 0.25 ml aliquot of the DPPC sheets with a 0.75 ml aliquot from the 200 mg/ml DSPC/Chol vesicle solution. The mixture was then briefly heated in a water bath at 46° C. for 20 minutes, and imaged using freeze-fracture. As indicated by FIG. 10, encapsulation of vesicles was successful.

The density of vesicles inside and outside of the IFVs was roughly equal. This type of encapsulation was carried out using different vesicle densities, and in every case vesicle density inside and outside the IFV shell was roughly equivalent. Furthermore, this type of encapsulation was successfully carried out using IFV shells of different composition and number of bilayers. Evidently, the encapsulation of vesicles was driven by the high volume fraction of vesicles, and not any vesicle-sheet interaction, whether specific (biotin/avidin), or non-specific (electrostatic/Van der Waals). The interior vesicles could also be charged, by addition of cationic or anionic lipids, without affecting the overall process.

Figure 11:
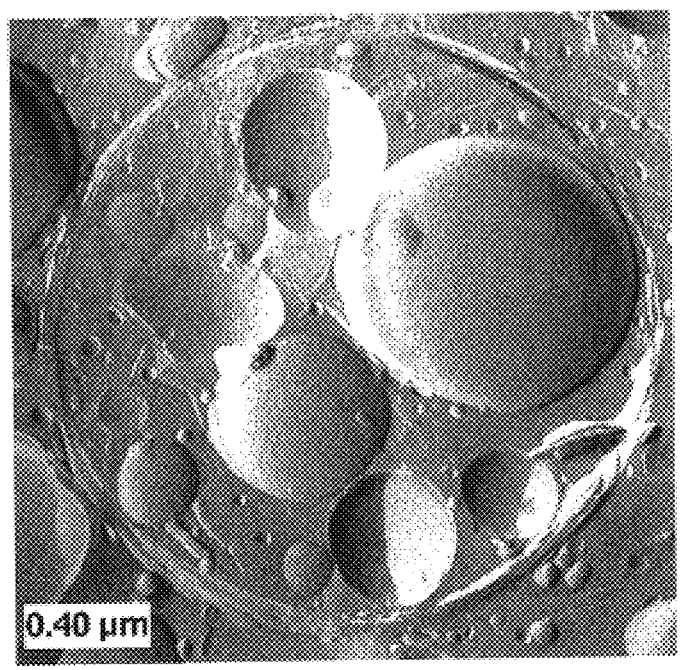
FIG. 11 is a TEM image of a vesosome formed by adding free vesicles to a solution of interdigitated sheets made of DPPC/Chol (97.5/2.5 molar ratio) at 3M EtOH, as described in Example 3, infra. Typical structures of this lipid mixture are vesosomes with multiple smaller vesicle structures inside.

The number and size of the IFV structures can be controlled by varying the cholesterol and ethanol concentrations. In FIG. 11, interdigitated sheets were made using 0.5 ml of a 50 nm DPPC/Chol (97.5/2.5 molar ratio) vesicle solution (25 mg/ml) fused by adding 0.106 ml of ethanol. The sheets were washed and diluted to a final concentration of 25 mg/ml. An 0.5 ml aliquot of the sheet solution was added to a 0.5 ml aliquot of a 50 nm DSPC/Chol 2:1 vesicle solution (concentration 50 mg/ml). As described before, the mixture was heated in a water bath at 46° C. for 20 minutes. The TEM images revealed IFVs structures with multiple smaller LUVs (large unilamellar vesicles) inside. These multi-compartmental IFVs were typical structures formed when heating interdigitated sheets made at this DPPC/Chol ratio. Free DSPC/Chol vesicles were encapsulated at a density equal to that of the cholesterol containing sheets in the solution. The outer IFV shell is typically more multilamellar than pure DPPC formed IFV structures. In FIG. 11, the free vesicles were added at a concentration considerably less than in the solutions shown in FIG. 10 (25 mg/ml final vesicle concentration in FIG. 11 as opposed to 150 mg/ml final vesicle concentration in FIG. 10). As before, vesicle density was equivalent inside and outside of the IFV structures. The encapsulation procedure was independent of the IFV composition.

The above procedures provide novel methods of efficiently encapsulating aggregates or free vesicles inside a second outer continuous bilayer. The encapsulation process was viable to encapsulating a variety of containment units. The nature of IFV formation also allowed for the outer bilayer membrane to be composed of varying lipid compositions. In these examples, the processes shown were carried out using DPPC, and DPPC/Chol mixtures, but encapsulation can also be carried out with other lipid mixtures, such as DPPC/cholesterol/stearylamine, DPPC/cholesterol/DPPG, DLPC, DPPC/POPC/cholesterol, and DPPC/cholesterol//biotinX-DHPE.

Controlling Vesosome Size

Figure 12:
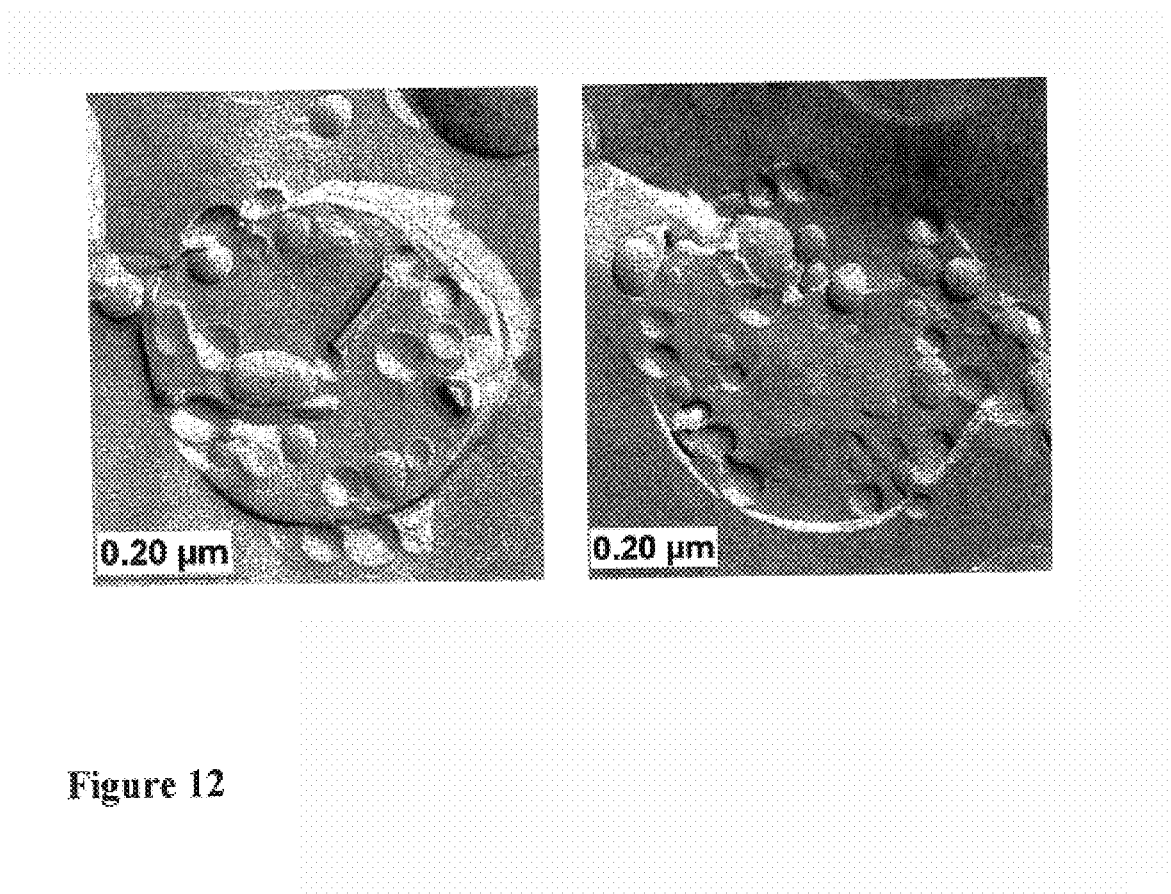
FIG. 12 depicts TEM images of monodisperse, reduced size vesosomes formed by extruding the vesosomes formed by the process shown in FIGS. 10 and 11, as described in Example 3, infra.

For intravenous use, several investigators have found that a maximum diameter of any vesicular structure should be 300 nm or less [D. D. Lasic, *Liposomes: From Physics to Applications* (Elsevier, Amsterdam (1993); T. M. Allen, *Current Opinion in Colloid and Interface Science* 1, 645 (1996)] to minimize uptake by the immune system. It was found that extrusion of the vesosome structure made by encapsulating free vesicles (FIGS. 10, 11) could reduce the size of the vesosomes, while maintaining the vesicle within a vesicle structure shown in FIG. 12. Vesicle density was equivalent inside and outside of the vesosome. This encapsulation procedure appeared to be independent of the IFV composition. The 50 nm interior vesicles were unaffected by the extrusion process. This allows for use of the vesosome as an intravenous delivery system with enhanced permeability control. The internal vesicle membranes can be constructed of any suitable lipid mixture including cationic or anionic lipids. This final sizing step, if performed with sufficiently small filters (0.22 micron) can also act as a sterilization step.

Separation of Vesosomes from Unencapsulated Vesicles

Figure 13:
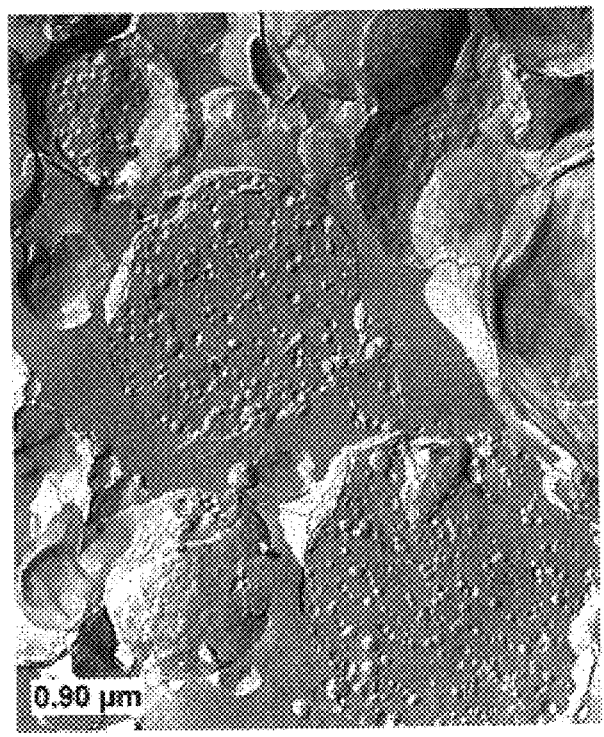
FIG. 13 shows the vesosomes and unencapsulated vesicles shown in FIGS. 10 and 11 were separated by centrifugation at 1700 rpm for 3 minutes in a benchtop centrifuge, as described in Example 3, infra.

Separating the vesosomes from unencapsulated vesicles can be done by gentle centrifugation. Quantitative separation of the encapsulated vesosomes from the unencapsulated vesicles was achieved by centrifuging for short periods (1–10 minutes) at speeds ranging from 1000–3000 rpm in a benchtop centrifuge as shown in FIG. 13. The supernatant was removed from the pelleted vesosomes and can be recycled to improve the overall efficiency of encapsulation. Separation by centrifugation may be done before, or after, the sizing step above. The speed of rotation was optimized to insure minimal damage to or fusion of the vesosomes.

Additional Modifications and Variations of the Invention

The presented invention allows for a number of variations in the methods described above. The exact composition of the encapsulated containment units, for example, vesicles, is not important and the vesicles can be composed of a variety of different lipid compositions and lipid mixtures. The vesicles can be prepared either through the procedures outlined in the patent, or through any other vesicle preparation techniques. Detergent dialysis, sonication, spontaneous vesicle preparations, and reverse phase evaporation, are all possible methods that can be used for vesicle preparation [Lasic, D. D., *Liposomes*, supra].

The methods of the invention allow for the encapsulation of free vesicles or vesicle aggregates. Both sized and massive aggregate structures can be used by controlling the stoichiometry of the ligands and receptors as described in [E. Kisak, et al. *Langmuir* 16, 2825 (2000)]. Sized aggregates can be prepared by controlling the ligand to receptor stoichiometry or by extruding massive aggregates [S. A. Walker, et al., *Nature* 387, 61 (1997)]. Aggregates can be produced by using a variety of interactions including, biotin-DHPE or biotin-X-DHPE with avidin or streptavidin, GM1 with peanut agglutinin or other ligand-receptor or antigen-antibody interactions.

Vesicle and vesicles aggregates can be loaded with a variety of different drugs or agents. Vesicles can also be loaded with magnetic particles, or can be complexed with proteins and DNA. The composition of the interior vesicle membrane, containment unit, colloidal particle, or biological macromolecule is unimportant to its encapsulation.

The encapsulating bilayer membranes can also be varied, although not as arbitrarily as the encapsulated vesicles. Any number of lipid membranes that form IFVs can be used; these structures can be controlled by changing ethanol concentrations used to make the sheets, and by controlling the concentration of the bilayer sheets. Other multi-compartmental structures can be used by controlling lipid composition, as shown in FIG. 11 for DPPC/cholesterol mixtures. The encapsulation of containment units appears to be unaffected by the composition of the sheets or the molarity of the ethanol used to make the sheets. The sheets can encapsulate vesicles with or without the use of biotin and streptavidin. The vesosome structure can be loaded with tethered polymers, such as polyethylene glycol, to shield the vesosome from macrophages. Furthermore, the sheets can also be loaded with specific targeting agents, such as antibodies, to link to particular tissues in the body.

The size of the vesosome can be controlled by chemical or mechanical means. Control of the IFV's size can be gained by altering the lipid composition and ethanol concentration used to fuse the vesicles.

Advantages of the vesosome over conventional drug delivery systems are discussed in Walker et al. [S. A. Walker, et al., *Nature* 387, 61 (1997)]. The vesosome structure divides necessary functions between two membranes rather than relying on one single membrane. The two membranes of the outer bilayer and the vesicles can be composed of entirely different lipid compositions allowing for a variety of different vesosome structures. The exterior bilayer membrane can be used as a "shield" layer to protect the vesosome from rapid bloodstream removal. This layer can be loaded with polymers and targeting agents. The interior vesicle membranes can be composed of lipid mixtures that are efficient at encapsulating drugs and controlling the release rate. Since these vesicles are shielded from the bloodstream, they can be composed of a variety of compositions that can not be used in conventional liposomes due to rapid clearance. Furthermore, these vesosomes can carry a mixture of different interior vesicles, colloidal particles, or biological macromolecules to deliver multiple drug components at once.

The new encapsulation procedure described herein is highly efficient. It does not rely on any specific interaction between the encapsulating bilayer membrane and the containment unit. Therefore, the methods can be easily expanded to encapsulate not only vesicles, but also polymer structures, DNA complexes, and protein structures. The methods do not require the use of crosslinking molecules, which may elicit an immune response. Almost any structure that can be dispersed in an aqueous solution is readily encapsulated with this procedure. The yield of encapsulated material is dramatically higher than in previous methods, and it is possible to recover any unencapsulated material during the separation process and recycle to minimize waste.

In summary, the methods and compositions of the invention provided herein take advantage of a number of new features including: 1.) the making of sized vesicle aggregates through controlled ligand-receptor stoichiometry [E. Kisak, et al. *Langmuir* 16, 2825 (2000]; 2.) encapsulating vesicles inside a second membrane using IFV vesicles; 3) separation of vesosomes from vesicles using centrifugation; and 4) size control of vesosomes by extrusion through filters.

What is claimed:

1. A composition comprising a bilayer membrane structure and multiple containment units, wherein the bilayer membrane structure encapsulates the multiple containment units, and wherein the bilayer membrane structure is distinct from the multiple containment units.

2. The composition of claim 1, wherein the containment units are aggregated within the bilayer membrane structure.

3. The composition of claim 1, wherein the bilayer membrane structure is generated from interdigitated sheets and is distinct from the multiple containment units.

4. The composition of claim 1, wherein the bilayer membrane structure comprises a ligand or receptor.

5. The composition of claim 1, wherein the membrane of the containment units comprises a ligand or receptor.

6. The composition of claim 2, wherein the aggregation of the containment units is selected from the group consisting of massive and quenched aggregates.

7. The composition of claim 2, wherein the aggregation of the containment units is selected from the group consisting of ligand-receptor interaction, antibody-antigen interaction, electrostatic interaction, and covalent chemical interaction.

8. The composition of claim 1, wherein the multiple containment units enclose an agent selected from the group consisting of a therapeutic agent, a diagnostic agent and an imaging agent.

9. A method for delivering a therapeutic agent to a target site which comprises introducing the composition of claim 8, wherein the containment units enclose a therapeutic agent, to the target site under suitable conditions such that the therapeutic agent is released therefrom.

10. The method of claim 9, wherein the composition is introduced by intramuscular injection, intravenous injection, oral administration, pulmonary adsorption, rectal, nasal, oral, ocular, vaginal, or urethral administration, subcutaneous injection, sublingual administration, or topical application.

11. A vesosome having a bilayer structure and multiple containment units, the bilayer structure encapsulating the multiple containment units, wherein the bilayer structure is distinct from the multiple containment units.

12. The vesosome of claim 11, wherein the bilayer structure is generated from interdigitated sheets and is distinct from the multiple containment units.

13. The vesosome of claim 11, wherein the multiple containment units are aggregated within the bilayer structure.

14. The composition of claim 11, wherein the bilayer membrane structure comprises a ligand or receptor.

15. The composition of claim 11, wherein the membrane of the containment units comprises a ligand or receptor.

16. The composition of claim 13, wherein the aggregation of the containment units is selected from the group consisting of massive and quenched aggregates.

17. The composition of claim 13, wherein the aggregation of the containment units is selected from the group consisting of ligand-receptor interaction, antibody-antigen interaction, electrostatic interaction and covalent chemical interaction.

18. The vesosome of claim 11, wherein the multiple containment units are of different size.

19. The vesosome of claim 11, wherein the multiple containment units are of the same size.

20. The vesosome of claim 11, wherein the multiple containment units enclose an agent selected from the group consisting of a therapeutic agent, a diagnostic agent and an imaging agent.

21. A method for encapsulating multiple containment units within a bilayer structure, to form a vesosome, comprising: mixing aggregated multiple containment units and open lipid bilayers in a solution under suitable conditions so that the open bilayers transform to create a bilayer structure that encapsulates the aggregated multiple containment units.

22. The method of claim 21, wherein the open lipid bilayers are interdigitated sheets.

23. The method of claim 21, wherein the open lipid bilayer comprises a ligand or receptor.

24. The method of claim 21, wherein the membrane of the containment units comprises a ligand or receptor.

25. The method of claim 21, wherein the aggregation of the containment units is selected from the group consisting of massive and quenched aggregates.

26. A method for delivering a therapeutic agent to a target site that comprises introducing the vesosome of claim 20, wherein the containment units enclose a therapeutic agent, to the target site under conditions so that the therapeutic agent is released therefrom.

27. The method of claim 26, wherein the vesosome is introduced by intramuscular injection, intravenous injection, oral administration, pulmonary adsorption, rectal, nasal, oral, ocular, vaginal, or urethral administration, subcutaneous injection, sublingual administration or topical application.

28. The method of claim 9 or 26, wherein the therapeutic agent is a drug acting at synaptic and/or neuroeffector junctional sites.

29. The method of claim 28, wherein the drug is selected from the group consisting of a neurohumoral transmitter, a cholinergic agonist, an anticholinesterase agent, an antimuscarinic drug, an agent acting at the neuromuscular junction and autonomic ganglia, a catecholamine, a sympathomimetic drug and an adrenergic receptor antagonist.

30. The method of claim 9 or 26, wherein the therapeutic agent is a drug acting on the CNS.

31. The method of claim 30, wherein the drug is selected from the group consisting of an antipsychotic drug, a neuroleptic drug, tricyclic antidepressants, monoamine oxidase inhibitors, lithium salts, and benzodiazepines.

32. The method of claim 9 or 26, wherein the therapeutic agent is a drug which reduces inflammation.

33. The method of claim 32, wherein the drug is selected from the group consisting of antagonists of histamines, bradykinins, 5-hydroxytryptaminse; lipid-derived autacoids; methylxanthines, cromolyn sodium and analgesic-antipyretics.

34. The method of claim 9 or 26, wherein the therapeutic agent is a drug which affects renal function and electrolyte metabolism.

35. The method of claim 34, wherein the drug is selected from the group consisting of diuretics and inhibitors of tubular transport of organic compounds.

36. The method of claim 9 or 26, wherein the therapeutic agent is a drug which affects cardiovascular function.

37. The method of claim 36, wherein the drug is selected from the group consisting of renin and angiotensin; organic nitrates, calcium-channel blockers and beta-adrenergic antagonists; antihypertensive agents, digitalis, antiarrhythmic drugs, and drugs used in the treatment of hyperlipoproteinemias.

38. A method for regulating the size of multiple containment unit aggregates comprising:
  a. preparing multiple containment units comprising a ligand on the surface of the multiple containment units;
  b. determining the ratio of the ligands on the surface of the multiple containment units to the receptors, for the ligand, in solution; and
  c. combining the multiple containment units of step (a) with the receptors in the amount so determined in step (b) thereby resulting in the aggregated multiple containment units having a desired size.

39. A method for regulating the size of multiple containment unit aggregates comprising:
  a. preparing multiple containment units comprising antigen on the surface of the multiple containment units;
  b. determining the ratio of the antigen on the surface of the multiple containment units to antibody in the solution; and
  c. combining the multiple containment units of step (a) with the antibody in the amount so determined in step (b) thereby resulting in the aggregated multiple containment units having a desired size.

* * * * *